US006470207B1

(12) United States Patent
Simon et al.

(10) Patent No.: US 6,470,207 B1
(45) Date of Patent: Oct. 22, 2002

(54) NAVIGATIONAL GUIDANCE VIA COMPUTER-ASSISTED FLUOROSCOPIC IMAGING

(75) Inventors: David A. Simon; Kurt R. Smith, both of Boulder, CO (US); Kevin T. Foley, Memphis, TN (US)

(73) Assignee: Surgical Navigation Technologies, Inc., Louisville, CO (US)

( * ) Notice: Subject to any disclaimer, the term of this patent is extended or adjusted under 35 U.S.C. 154(b) by 0 days.

(21) Appl. No.: 09/274,972

(22) Filed: Mar. 23, 1999

(51) Int. Cl.[7] ................................................. A61B 5/00
(52) U.S. Cl. ........................ 600/426; 600/427; 378/207
(58) Field of Search ................................ 600/425, 426, 600/427, 428; 378/16, 19, 20, 62, 96, 97, 108, 114, 117, 145, 205, 207; 250/370.08, 370.09, 370.1

(56) References Cited

U.S. PATENT DOCUMENTS

| 1,576,781 A | 3/1926 | Philips |
| 1,735,726 A | 11/1929 | Bornhardt |
| 2,407,845 A | 9/1946 | Nemeyer ..................... 116/124 |
| 2,650,588 A | 9/1953 | Drew .......................... 128/92 |

(List continued on next page.)

FOREIGN PATENT DOCUMENTS

| CA | 964149 | 3/1975 | |
| DE | 3042343 | 6/1982 | |
| EP | 350996 | 1/1990 | |
| EP | 0 581 704 A1 | 7/1993 | ............ A61B/8/14 |
| FR | 79 04241 | 2/1979 | ............ A61B/17/18 |
| WO | WO 88/09151 | 12/1988 | ............ A61B/19/00 |
| WO | WO 9103982 | 4/1991 | |
| WO | WO 91/04711 | 4/1991 | ............ A61B/19/00 |
| WO | WO 91/07726 | 5/1991 | ............ G06F/15/72 |
| WO | WO 92/06645 | 4/1992 | |
| WO | WO 94/23647 | 10/1994 | ............ A61B/5/05 |
| WO | WO 94/24933 | 11/1994 | |
| WO | WO 96/11624 | 4/1996 | |
| WO | WO 98/38908 | 9/1998 | ............ A61B/5/00 |

OTHER PUBLICATIONS

André Guéziec et al., "Registration of Computer Tomography Data to a Surgical Robot Using Fluorscopy: A Feasibility Study," Computer Science/Mathematics, Sep. 27, 1996, 6 pages.

Ali Hamadeh et al., "Towards Automatic Registration Between CT and X–ray Images: Cooperation Between 3D/2D Registration and 2D Edge Detection," MRCAS '95, pp. 39–46.

(List continued on next page.)

*Primary Examiner*—Ruth S. Smith
(74) *Attorney, Agent, or Firm*—Harness, Dickey & Pierce, P.L.C.

(57) ABSTRACT

Digital x-ray images taken before a surgical procedure by a fluoroscopic C-arm imager are displayed by a computer and overlaid with graphical representations of instruments be used in the operating room. The graphical representations are updated in real-time to correspond to movement of the instruments in the operating room. A number of different techniques are described that aid the physician in planning and carrying out the surgical procedure.

23 Claims, 16 Drawing Sheets

U.S. PATENT DOCUMENTS

| | | | |
|---|---|---|---|
| 2,697,433 A | 12/1954 | Sehnder .................... 128/83 |
| 3,016,899 A | 1/1962 | Stenvall .................... 128/348 |
| 3,017,887 A | 1/1962 | Heyer ...................... 128/348 |
| 3,061,936 A | 11/1962 | Dobbeleer ................. 33/174 |
| 3,073,310 A | 1/1963 | Mocarski ................... 128/303 |
| 3,294,083 A | 12/1966 | Alderson .................... 128/2 |
| 3,367,326 A | 2/1968 | Frazier ..................... 128/92 |
| 3,577,160 A | 5/1971 | White ...................... 250/59 |
| 3,702,935 A | 11/1972 | Carey et al. ............... 250/58 |
| 3,704,707 A | 12/1972 | Halloran .................... 128/92 |
| 3,941,127 A | 3/1976 | Froning ..................... 128/215 |
| 4,037,592 A | 7/1977 | Kronner |
| 4,052,620 A * | 10/1977 | Brunnett .................... 250/445 |
| 4,117,337 A | 9/1978 | Staats ..................... 250/445 T |
| 4,202,349 A | 5/1980 | Jones ....................... 128/689 |
| 4,358,856 A | 11/1982 | Stivender et al. .......... 378/167 |
| 4,368,536 A * | 1/1983 | Pfeiler ...................... 378/19 |
| 4,403,321 A | 9/1983 | DiMarco |
| 4,418,422 A | 11/1983 | Richter et al. |
| 4,485,815 A | 12/1984 | Amplatz |
| 4,543,959 A | 10/1985 | Sepponen ................. 128/653 |
| 4,621,628 A | 11/1986 | Bludermann |
| 4,625,718 A | 12/1986 | Olerud et al. |
| 4,651,732 A | 3/1987 | Frederick .................. 128/303 R |
| 4,653,509 A | 3/1987 | Oloff et al. ................. 128/749 |
| 4,706,665 A | 11/1987 | Gouda ..................... 128/303 B |
| 4,722,056 A | 1/1988 | Roberts et al. ............. 364/413 |
| 4,722,336 A | 2/1988 | Kim et al. ................. 128/303 |
| 4,727,565 A | 2/1988 | Ericson ..................... 378/205 |
| 4,737,921 A | 4/1988 | Goldwasser et al. ........ 364/518 |
| 4,750,487 A | 6/1988 | Zanetti |
| 4,771,787 A | 9/1988 | Wurster et al. ........... 128/660.03 |
| 4,791,934 A | 12/1988 | Brunnett .................... 128/653 |
| 4,797,907 A | 1/1989 | Anderton |
| 4,803,976 A | 2/1989 | Frigg et al. ................ 128/92 |
| 4,821,206 A | 4/1989 | Arora ....................... 364/513 |
| 4,845,771 A * | 7/1989 | Wislocki et al. ............. 378/97 |
| 4,991,579 A | 2/1991 | Allen ...................... 128/653 R |
| 5,013,317 A | 5/1991 | Cole et al. |
| 5,027,818 A | 7/1991 | Bova et al. ............... 128/653 R |
| 5,030,222 A | 7/1991 | Calandruccio et al. ........ 606/96 |
| 5,031,203 A | 7/1991 | Trecha ...................... 378/205 |
| 5,059,789 A | 10/1991 | Salcudean ................ 250/206.1 |
| 5,079,699 A | 1/1992 | Tuy et al. ................ 364/413.22 |
| 5,094,241 A | 3/1992 | Allen ...................... 128/653.1 |
| 5,097,839 A | 3/1992 | Allen ...................... 128/653.1 |
| 5,107,843 A | 4/1992 | Aarnio et al. ........... 128/662.05 |
| 5,119,817 A | 6/1992 | Allen ...................... 128/653.1 |
| 5,142,930 A | 9/1992 | Allen et al. .................. 74/469 |
| 5,178,164 A | 1/1993 | Allen ...................... 128/898 |
| 5,178,621 A | 1/1993 | Cook et al. |
| 6,186,174 B1 | 2/1993 | Schlondorff et al. |
| 5,198,877 A | 3/1993 | Schulz ...................... 356/375 |
| 5,211,164 A | 5/1993 | Allen ...................... 128/653.1 |
| 5,212,720 A | 5/1993 | Landi et al. ............... 378/206 |
| 5,219,351 A | 6/1993 | Teubner et al. ............ 606/130 |
| 5,233,990 A * | 8/1993 | Barnea ...................... 600/407 |
| 5,249,581 A | 10/1993 | Horbal et al. ............. 128/664 |
| 5,251,127 A | 10/1993 | Raab ...................... 364/413.13 |
| 5,295,483 A | 3/1994 | Nowacki et al. ........ 128/660.03 |
| 5,305,203 A | 4/1994 | Raab ...................... 364/413.13 |
| 5,309,913 A | 5/1994 | Kormos et al. ........... 128/653.1 |
| 5,320,111 A | 6/1994 | Livingston |
| 5,333,168 A | 7/1994 | Fernandes et al. |
| 5,368,030 A | 11/1994 | Zinreich et al. |
| 5,383,454 A | 1/1995 | Bucholz |
| 5,389,101 A | 2/1995 | Heilbrun et al. |
| 5,399,146 A | 3/1995 | Nowacki et al. ............. 601/4 |
| 5,400,384 A | 3/1995 | Fernandes et al. |
| 5,402,801 A | 4/1995 | Taylor ..................... 128/898 |
| 5,408,409 A | 4/1995 | Glassman et al. |
| 5,426,683 A | 6/1995 | O'Farrell, Jr. et al. |
| 5,426,687 A | 6/1995 | Goodall et al. ............ 378/206 |
| 5,427,097 A | 6/1995 | Depp |
| RE35,025 E | 8/1995 | Anderton |
| 5,444,756 A * | 8/1995 | Pai et al. .................. 378/98.8 |
| 5,446,548 A | 8/1995 | Gerig et al. |
| 5,447,154 A | 9/1995 | Cinquin et al. .......... 128/653.1 |
| 5,448,610 A * | 9/1995 | Yamamoto et al. ........... 378/19 |
| 5,478,341 A | 12/1995 | Cook et al. |
| 5,478,343 A | 12/1995 | Ritter |
| 5,483,961 A | 1/1996 | Kelly et al. ............... 128/653.1 |
| 5,490,196 A | 2/1996 | Rudich et al. ............. 378/101 |
| 5,494,034 A | 2/1996 | Schlondorff et al. ..... 128/653.1 |
| 5,503,416 A | 4/1996 | Aoki et al. |
| 5,515,160 A | 5/1996 | Schulz et al. .............. 356/241 |
| 5,517,990 A | 5/1996 | Kalfas et al. ............. 128/653.1 |
| 5,531,227 A | 7/1996 | Schneider ................ 128/653.1 |
| 5,531,520 A | 7/1996 | Grimson et al. ............ 382/131 |
| 5,568,809 A | 10/1996 | Ben-haim ................. 128/656 |
| 5,572,999 A | 11/1996 | Funda et al. ............. 128/653.1 |
| 5,583,909 A | 12/1996 | Hanover |
| 5,588,430 A | 12/1996 | Bova et al. .............. 128/653.1 |
| 5,596,228 A | 1/1997 | Anderton et al. |
| 5,603,318 A | 2/1997 | Heilbrun et al. |
| 5,617,462 A | 4/1997 | Spratt |
| 5,617,857 A | 4/1997 | Chader et al. ........... 128/653.1 |
| 5,619,261 A | 4/1997 | Anderton |
| 5,622,170 A | 4/1997 | Schulz ..................... 128/653.1 |
| 5,627,873 A | 5/1997 | Hanover et al. |
| 6,630,431 | 5/1997 | Taylor ....................... 128/897 |
| 5,638,819 A * | 6/1997 | Manwaring et al. ........ 600/407 |
| 5,642,395 A | 6/1997 | Anderton et al. |
| 5,647,361 A | 7/1997 | Damadian ................. 128/683.2 |
| 5,662,111 A | 9/1997 | Cosman .................... 128/653.1 |
| 5,664,001 A * | 9/1997 | Tachibana et al. ......... 378/98.8 |
| 5,676,673 A | 10/1997 | Ferre et al. ................. 606/130 |
| 5,682,886 A | 11/1997 | Delp et al. ................ 128/653.1 |
| 5,690,108 A | 11/1997 | Chakeres |
| 5,695,500 A | 12/1997 | Taylor et al. ................ 606/130 |
| 5,695,501 A | 12/1997 | Carol et al. ................. 606/130 |
| 5,711,299 A | 1/1998 | Manwaring et al. ..... 128/653.1 |
| 5,748,767 A | 5/1998 | Raab |
| 5,749,362 A | 5/1998 | Funda et al. ............. 128/653.1 |
| 5,755,725 A | 5/1998 | Druais ...................... 606/130 |
| 5,769,789 A | 6/1998 | Wang et al. |
| 5,769,861 A | 6/1998 | Vilsmeier ................... 606/130 |
| 5,772,594 A * | 6/1998 | Barrick ..................... 600/407 |
| 5,795,294 A | 8/1998 | Luber et al. ................ 600/407 |
| 5,799,055 A | 8/1998 | Peshkin et al. .............. 378/42 |
| 5,800,535 A | 9/1998 | Howard, III ................. 623/10 |
| 5,802,719 A | 9/1998 | O'Farrell, Jr. et al. |
| 5,823,192 A * | 10/1998 | Kalend et al. .............. 600/427 |
| 5,823,958 A | 10/1998 | Truppe ...................... 600/426 |
| 5,828,725 A | 10/1998 | Levinson |
| 5,833,608 A | 11/1998 | Acker ...................... 600/409 |
| 5,834,759 A | 11/1998 | Glossop ................... 250/203.1 |
| 5,836,954 A | 11/1998 | Heilbrun et al. |
| 5,848,967 A | 12/1998 | Cosman .................... 600/426 |
| 5,851,183 A | 12/1998 | Bucholz ..................... 600/425 |
| 5,868,675 A | 2/1999 | Henrion et al. ............ 606/424 |
| 5,871,445 A | 2/1999 | Bucholz |
| 5,871,487 A | 2/1999 | Warner et al. ............. 606/130 |
| 5,891,034 A | 4/1999 | Bucholz |
| 5,891,157 A | 4/1999 | Day et al. .................. 606/130 |
| 5,904,691 A | 5/1999 | Barnett et al. ............ 606/130 |
| 5,920,395 A | 7/1999 | Schulz ...................... 356/375 |
| 5,921,992 A | 7/1999 | Costales et al. ............ 606/130 |
| 5,923,727 A * | 7/1999 | Navab ....................... 378/207 |
| 5,951,475 A * | 9/1999 | Gueziec et al. ............ 600/425 |
| 6,016,439 A * | 1/2000 | Acker ........................ 600/411 |

| | | | | |
|---|---|---|---|---|
| 6,050,724 A | * | 4/2000 | Schmitz et al. | 378/205 |
| 6,139,183 A | * | 10/2000 | Graumann | 378/206 |
| 6,149,592 A | * | 11/2000 | Yanof et al. | 600/427 |
| 6,167,296 A | * | 12/2000 | Shahidi | 600/427 |

OTHER PUBLICATIONS

L. Lemieux et al., "A Patient–to–Computer–Tomography Image Registration Method Based on Digitally Reconstructed Radiographs," Med. Phys. 21 (11), Nov. 1994, pp. 1749–1760.

Lisa M. Gottesfeld Brown et al., "Registration of Planar Film Radiographs with Computer Tomography," Proceedings of MMBIA, Jun. '96, pp. 42–51.

W.J. Viant et al., "A Computer Assisted Orthopaedic System for Distal Locking of Intramedullary Nails," Proc. of MediMEC '95, Bristol, 1995, pp. 86–91.

R. Phillips et al., "Image Guided Orthopaedic Surgery Design and Analysis," Trans Inst MC, vol. 17, No. 5, 1995, pp. 251–264.

R. Hofstetter et al., "Fluoroscopy Based Surgical Navigation—Concept and Clinical Applications," Computer Assisted Radiology and Surgery, 1997, pp. 956–960.

Jacques Feldmar et al., "3D–2D Projective Registration of Free–Form Curves and Surfaces," Rapport de recherche (Inria Sophia Antipolis), 1994, pp. 1–44.

C. Brack et al., "Accurate X–ray Based Navigation in Computer–Assisted Orthopedic Surgery," CAR '98, pp. 716–722.

Leo Joskowicz et al., "Computer–Aided Image–Guided Bone Fracture Surgery: Concept and Implementation," CAR '98, pp. 710–715.

Ali Hamadeh et al., "Automated 3–Dimensional Computer Tomographic and Fluoroscopic Image Registration," Computer Aided Surgery (1998), 3:11–19.

Jürgen Weese, et al., "An Approach to 2D/3D Registration of a Vertebra in 2D X–ray Fluoroscopies with 3D CT Images," pp. 119–128.

P. Potamianos, et al., "Intra–Operative Imaging Guidance for Keyhole Surgey Mehtodology and Calibration," First International Symposium on Medical Robotics and Computer Assisted Surgery, Sep. 22–24, 1994, pp. 98–104.

G. Selvik, et al., "A Roentgen Stereophotogrammetric System," Acta Radiologica Diagnosis, 1983, pp. 343–352.

Pascal Phillippe Sautot, "Vissage Pediculaire Assiste Par Ordinateur," Sep. 20, 1994.

Stephane lavallee, et al., "Image guided operating robot: a clinical application in stereotactic neurosurgery," Proceedings of the 1992 IEEE Internation Conference on Robotics and Automation, May 1992, pp. 618–624.

P. Cinquin, et al., "Computer Assisted Medical Interventions," IEEE Engineering in Medicine and Biology, May/Jun. 1995, pp. 254–263.

P. Cinquin, et al., "Kinematic Study of Lumbar Spine Using Functional Radiographies and 3D/2D Registration," TIMC UMR 5525—IMAG.

P. Cinquin, et al., "Computer Assisted Spine Surgery: A Technique For Accurate Transpedicular Screw Fixation Using CT Data and a 3–D Optical Localizer," TIMC, Faculte de Medecine de Grenoble.

E. Frederick Barrick, "Journal of Orthopaedic Trauma: Distal Locking Screw Insertion Using a Cannulated Drill Bit: Technical Note," Raven Press, vol. 7, No. 3, 1993, pp. 248–251.

Bouazza–Marouf et al.; "Robotic–Assisted Internal Fixation of Femoral Fractures", IMECHE. pp. 51–58 (1995).

Barrick, Frederick E., et al., "Prophylactic Intramedullary Fixation of the Tibia for Stress Fracture in a Professional Athlete," Journal of Orthopaedic Trauma, vol. 6, No. 2, pp. 241–244 (1992).

Barrick, Frederick E., et al., "Technical Difficulties with the Brooker–Wills Nail in Acute Fractures of the Femur," Journal of Orthopaedic Trauma, vol. 6, No. 2, pp. 144–150 (1990).

Foley, K.T., The SteathStation™: Three–Dimensional Image–Interactive Guidance for the Spine Surgeon, Spinal Frontiers, Apr. 1996, pp. 7–9.

Mazier, B., Lavallée, S., Cinquin, P., Chirurgie de la Colonne Vertebrale Assistee par Ordinateur: Appication au Vissage Pediculaire, Innov. Tech. Bio. Med., vol. 11, No. 5, 1990, pp. 559–566.

Mazier, B., Lavallee, S., Cinquin, P., Computer Assisted Interventionist Imaging: Application to the Vertebral Column Surgery, Annual International Conference of the IEEE Engineering in Medicine and Biology Society, vol. 12, No. 1, 1990, pp. 0430–0431.

Lavallée, S., Cinquin, P., Demongeot, J., Benabid, A.L., Marque, I., Djaid, M., Computer Assisted Driving of a Needle into the Brain, Proceedings of the International Symposium: CAR 89, pp. 416–420.

Lavallée, S., Cinquin, P., Dermongeot, J., Benabid, A L., Marque, I., Djaid, M., Computer Assisted Interventionist Imaging: The Instance of Stereotactic Brain Surgery, North–Holland MEDINFO 89, Part 1, 1989, pp. 613–617.

Lavallée, S., A New System for Computer Assisted Neurosurgery, IEEE Engineering in Medicine & Biology Society 11$^{th}$ Annual International Conference, 1989, pp. 0926–0927.

Reinhardt, H.F., Landolt, H., CT–Guided "Real Time" Stereotaxy, ACTA Neurochirurgica, 1989.

Watanabe, E., Watanabe, T., Manaka, S., Mayanagi, Y., Takakura, K., Three–Dimensional Digitizer (Neuronavigator): New Equipment for Computed Tomography–Guided Stereotaxic Surgery, Surgical Neurology, vol. 27, No. 6, Jun. 1987, pp. 543–547.

Watanabe, H., Neuronavigator, Igaku–no–Ayumi, vol. 137, No. 6, May 10, 1986, pp. 1–4.

Roberts, D.W., Strohbehn, J.W., Hatch, J.F., Murray, W., Kettenberger, H., A frameless stereotaxic integration of computerized tomographic imaging and the operating microscope, J. Neurosurg., vol. 65, Oct. 1986, pp. 545–549.

Leksell, L., Jernberg, B., Stereotaxis and Tomography—A Technical Note, ACTA Neurochirurgica, vol. 52, 1980, pp. 1–7.

Hoerenz, P., The Operating Microscrope I. Optical Principles, Illumination Systems, and Support Systems, Journal of Microsurgery, vol. 1, 1980, pp. 364–369.

Hounsfield, G.N., Computerized transverse axial scanning (tomography): Part I. Description of system, British Journal of Radiology, vol. 46, No. 552, Dec. 1973, pp. 1016–1022.

Foley, K.T., Smith, K.R., Bucholz, R.D., Image–guided Intraoperative Spinal Localization, Intraoperative Neuroprotection, Chapter 19, 1996, pp. 325–340.

Henderson, J.M., Smith, K.R., Bucholz, R.D., An Accurate and Ergonomic Method of Registration for Image–guided Neurosurgery, Computerized Medical Imaging and Graphics, vol. 18, No. 4, Jul.–Aug. 1994, pp. 273–277.

Lavallée, S., Brunie, L., Mazier, B., Cinquin, P., Matching of Medical Images for Computed and Robot Assisted Surgery, IEEE EMBS, Orlando, 1991.

Smith, K.R., Bucholz, R.D., Computer Methods for Improved Diagnostic Image Display Applied to Stereotactic Neurosurgery, Automedical, vol. 14, 1992, pp. 371–382.

Adams, L., Knepper, A., Krybus, W., Meyer–Ebrecht, D., Pfeifer, G., Ruger, R., Witte, M., Aide au Reperage Tridimensionnel pour la Chirurgie de la Base du Crane, Innov. Tech. Biol. Med., vol. 13, No. 4, 1992, pp. 409–424.

Colchester, A.C.F., Hawkes, D.J., Information Processing in Medical Imaging, Lecture Notes in Computer Science, $12^{th}$ International Conference, IPMI, Jul. 1991, pp. 136–141.

Lavallée, S., Zseliski, R., Brunie, L., Matching 3–D Smooth Surfaces with Their 2–D Projections using 3–D Distance Maps, SPIE, vol. 1570, Geometric Methods in Computer Vision, 1991, pp. 322–336.

Clarysse, P., Gibon, D., Rousseau, J., Blond, S., Vasseur, C., Marchandise, X., A Computer–Assisted System for 3–D Frameless Localization in Stereotaxic MRI, IEEE Transactions on Medical Imaging, vol. 10, No. 4, Dec. 1991, pp. 523–529.

Champleboux, G., Utilisation de Fonctions Splines pour la Mise au Point D'un Capteur Tridimensionnel sans Contact, Quelques Applications Medicales, Jul. 1991.

Pelizzari, C.A., Chen, G.T.Y., Spelbring, D.R., Weichselbaum, R.R., Chen, C., Accurate Three–Dimensional Registration of CT, PET, and/or MR Images of the Brain, Journal of Computer Assisted Tomography, Jan./Feb. 1989, pp. 20–26.

Lavellée, S., Cinquin, P., Demongeot, J., Benabid, A.L., Marque, I., Djaïd, M., Computer Assisted Interventionist Imaging: The Instance of Stereotactic Brain Surgery, North–Holland MEDINFO 89, Part 1, 1989, pp. 613–617.

Lavallee, S., Cinquin, P., Demongeot, J., Benabid, A.L., Marque, I., Djaid, M., Computer Assisted Driving of a Needle into the Brain, Proceedings of the International Symposium CAR '89, Computer Assisted Radiology, 1989, pp. 416–420.

Levin, D.N., Hu, X., Tan, K.K., Galhotra, S., Pelizzari, C.A., Chen, G.T.Y., Beck, R.N., Chen, C., Cooper, M.D., Mullan, J.F., Hekmatpanah, J., Spire, J., The Brain: Integrated Three–dimensional Display of MR and PET Images, Radiology, vol. 172, No. 3, Sep. 1989, pp. 783–789.

Cinquin, P., Lavallee, S., Demongeot, J., Computer Assisted Medical Interventions, International Advanced Robotics Programme, Sep. 1989, pp. 63–65.

Gonzalez, R.C., Digital Image Fundamentals, Digital Image Processing, Second Edition, 1987, pp. 52–54.

Pelizzari, C.A., Chen, G.T.Y., Halpern, H., Chen, C.T., Cooper, M.D., No. 528—Three Dimensional Correlation of PET, CT and MRI Images, The Journal of Nuclear Medicine, vol. 28, No. 4, Apr. 1987, p. 682.

Foley, J.D., Van Dam, A., Fundamentals of Interactive Computer Graphics, The Systems Programming Series, Chapter 7, Jul. 1984, pp. 245–266.

Hatch, J.F., Reference–Display System for the Integration of CT Scanning and the Operating Microscope, Thesis, Thayer School of Engineering, Oct. 1984, pp. 1–189.

Kelly, P.J., Kall, B., Goerss, S., Alker, G.J., Jr., Precision Resection of Intra–Axial CNS Lesions by Ct–Based Stereotactic Craniotomy and Computer Monitored $CO_2$ Laser, Acta Neurochirurgica, vol. 68, 1983, pp. 1–9.

Gildenberg, P.L., Kaufman, H.H., Murthy, K.S., Calculation of Stereotactic Coordinates from the Computed Tomographic Scan, Neurosurgery, vol. 10, No. 5, May 1982, pp. 580–586.

Batnitzky, S., Price, H.I., Lee, K.R., Cook, P.N., Cook, L.T., Fritz, S.L., Dwyer, S.J., Watts, C., Three–Dimensional Computer Reconstructions of Brain Lesions from Surface Contours Provided by Computed Tomography: A Prospectus, Neurosurgery, vol. 11, No. 1, Part 1, 1982, pp. 73–84.

Rosenbaum, A.E., Lunsford, L.D., Perry, J.H., Computerized Tomography Guided Sterotaxis: A New Approach, Applied Neurophysiology, vol. 43, No. 3–5, 1980, pp. 172–173.

Jacques, S., Shelden, C.H., McCann, G.D., A Computerized Microstereotactic Method to Approach, 3–Dimensionally Reconstruct, Remove and Adjuvantly Treat Small CNS Lesions, Applied Neurophysiology, vol. 43, 1980, pp. 176–182.

Jacques, S., Shelden, C.H., McCann, G.D., Freshwater, D.B., Rand, R., Computerized three–dimensional stereotaxic removal of small central nervous system lesion in patients, J. Neurosurg., vol. 53, Dec. 1980, pp. 816–820.

Shelden, C.H., McCann, G., Jacques, S., Lutes, H.R., Frazier, R.E., Katz, R., Kuki, R., Development of a computerized microstereotaxic method for localization and removal of minute CNS lesions under direct 3–D vision, J. Neurosurg., vol. 52, 1980, pp. 21–27.

Lavallée, S., *VI Adaptation de la Methodologie a Quelques Applications Cliniques*, Chapitre VI, pp. 133–148.

* cited by examiner

202

204

NAVIGATIONAL GUIDANCE VIA COMPUTER-ASSISTED FLUOROSCOPIC IMAGING

RELATED APPLICATIONS

This disclosure is related to U.S. patent application Ser. No. 09/106,109, entitled "System and Methods for the Reduction and Elimination of Image Artifacts in the Calibration of X-Ray Imagers," filed on Jun. 29, 1998.

FIELD OF THE INVENTION

The present invention is directed generally to image guided surgery, and more particularly, to systems and methods for using one or more fluoroscopic X-ray images to assist in instiuent navigation during surgery.

DESCRIPTION OF THE RELATED ART

Modern diagnostic medicine has benefitted significantly from radiology, which is the use of radiation, such as x-rays, to generate images of internal body structures. In general, to create an x-ray image, x-ray beams are passed through the body and absorbed, in varying amounts, by tissues in the body. An x-ray image is created based on the relative differences in the transmitted x-ray intensities.

Techniques are known through which x-ray images are used to locate the real-time position of surgical instruments in the patient anatomy represented by the x-ray image without requiring x-rays to be continually taken. In one such system, as disclosed in U.S. Pat. No. 5,772,594 to Barrick, light emitting diodes (LEDs) are placed on a C-arm fluoroscope x-ray imager, on drill, and on a reference bar positioned on the bone to be studied. A three-dimensional optical digitizer senses the position of the LEDs, and hence the position of the drill, the C-arm fluoroscope, and the object bone. Based on this information, the real-time position of the drill in anatomy represented by the x-ray image is determined, and a corresponding representation of the drill in the x-ray image is displayed. This allows the surgeon to continually observe the progress of the surgery without necessitating additional x-ray images.

Surgical navigational guidance, as discussed above, can provide a tool for helping the physician perform surgery. It is an object ofthe present invention to provide several enhancements to traditional surgical navigational guidance techniques.

SUMMARY OF THE INVENTION

Objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

One aspect of the present invention is directed to an x-ray imaging device comprising a plurality of elements. In particular, the x-ray imaging device includes an x-ray source for generating cycles of x-ray radiation corresponding to an image acquisition cycle; an x-ray receiving section positioned so that x-rays emanating from the x-ray source enter the x-ray receiving section, the x-ray receiving section generating an image representing intensities of the x-rays entering the x-ray receiving section. Additionally, a computer is coupled to the x-ray receiving section and radiation sensors are located in a path of the x-rays emitted from the x-ray source. The radiation sensors detect the beginning and end of a radiation cycle and transmit the detected beginning and end of the radiation cycle to the computer.

Another imaging device consistent with the present invention includes a rotatable (C-arm support having first and second ends. The first end includes an x-ray source for initiating an imaging cycle and the second end includes an x-ray receiving section positioned so that x-rays emanating from the x-ray source enter the x-ray receiving section. The x-ray receiving section generates an image representing the intensities of the x-rays entering the x-ray receiving section. Further, a calibration and tracking target is included and a tracking sensor detects the position, in three-dimensional space, of the calibration and tracking target; and a computer is couples to the x-ray receiving section and the tracking sensor. The computer detects motion of the C-arm based on changes in the position detected by the tracking sensor.

Another aspect consistent with the present invention is directed to a surgical instrument navigation system. The system comprises a computer processor; a tracking sensor for sensing three-dimensional position information of a surgical instrument and transmitting the position information to the computer processor; a memory coupled to the computer processor, the memory including computer instructions that when executed by the computer processor cause the processor to generate an icon representing the surgical instrument and to overlay the icon on a pre-acquired x-ray image, the icon of the surgical instrument representing the real-time position of the surgical instrument projected into the pre-acquired x-ray image and the icon being generated as first representation when the surgical instrument is positioned such that it is substantially viewable in the plane of the pre-acquired image and the icon being generated as a second representation when the surgical instrument is positioned such that it is substantially perpendicular to the plane of the pre-acquired image. Finally, a display is coupled to the processor for displaying the generate icon superimposed on the pre-acquired image.

Yet another system consistent with the present invention comprises a computer processor and a tracking sensor for sensing three-dimensional position information of a surgical instrument and transmitting the position information to the computer processor. A memory is coupled to the computer processor, the memory including computer instructions that when executed by the computer processor cause the processor to generate an icon representing the surgical instrument positioned in a pre-acquired image of a patient's anatomy, the icon of the surgical instrument including a first portion corresponding to an actual position of the surgical instrument and a second portion corresponding to a projection of the surgical instrument along a line given by a current trajectory of the surgical instrument. A display is coupled to the processor for displaying the generated icon superimposed on the pre-acquired image.

Still further, another surgical instrument navigation system consistent with the present invention comprises a rotatable C-arm including an x-ray source and an x-ray receiving section for acquiring x-ray images of a patient, the C-arm being rotatable about one of a plurality of mechanical axes. A computer processor is coupled to the rotatable C-arm and a memory is coupled to the computer processor. The memory stores the x-ray images acquired by the rotatable C-arm and computer instructions that when executed by the computer processor cause the computer processor to generate a line representing a projection of a plane parallel to one of the plurality of the mechanical axes of the C-arm into the x-ray image, the line enabling visual alignment of the one of the plurality of mechanical axes of the C-arm with an axis relating complimentary image views. A display is coupled to the processor for displaying the generated line superimposed on the x-ray image.

Yet another system consistent with the present invention is for defining a surgical plan and comprises an x-ray imaging device; a surgical instrument; a tracking sensor for detecting the position, in three-dimensional space, of the surgical instrument; a computer processor or in communication with the tracking sensor for defining a point in a virtual x-ray imaging path is the three-dimensional location of the surgical instrument, the point being outside of a true x-ray imaging path of the x-ray imaging device, the computer processor translating position of the surgical instrument within the virtual x-ray imaging path to a corresponding position in the true x-ray imaging path; and a display coupled to the processor for displaying a pre-acquired x-ray image overlaid with an iconic representation of the surgical instrument, the position of the iconic representation of the surgical instrument in the pre-acquired x-ray image corresponding to the translated position of the surgical instrument.

Yet another system consistent with the present invention for defining a surgical plan comprises a combination of elements. The elements include an x-ray imaging device; a surgical instrument; a tracking sensor for detecting the position, in three-dimensional space, of the surgical instrument; a computer processor in communication with the tracking sensor for calculating a projection of the trajectory of the surgical instrument a distance ahead of the actual location of the surgical instrument; and a display coupled to the processor for displaying a pre-acquired x-ray image overlaid with an iconic representation of the surgical instrument and the calculated projection of the trajectory of the surgical instrument.

Yet another system consistent with the present invention is for aligning a first bone segment with a second bone segment in a patient. The system comprises a first tracking marker attached to the first bone segment and a second tracking marker attached to the second bone segment. A tracking sensor detects the relative position, in three-dimensional space, of the first and second tracking markers. A computer delineates boundaries of images of the first and second bone segments in a pre-acquired x-ray image and when the second bone segment is moved in the patient, the computer correspondingly moves the delineated boundary of the second bone segment in the x-ray image. A display is coupled to the computer and displays the pre-acquired x-ray image overlaid with representations of the delineated boundaries of the first and second bone segments.

Yet another system consistent with the present invention is directed to a system for placing a surgical implant into a patient. The system comprises a computer processor; means for entering dimensions of the implant; a tracking sensor for sensing three-dimensional position information of a surgical instrument on which the surgical implant is attached, the tracking sensor transmitting the position information to the computer processor; and a memory coupled to the computer processor, the memory including computer instructions that when executed by the computer processor cause the processor to generate an icon representing the surgical instrument and the attached surgical implant, and to overlay the icon on a pre-acquired two-dimensional x-ray image, the icon of the surgical instrument representing the real-time position of the surgical instrument relative to the pre-acquired two-dimensional x-ray image.

In addition to the above mention devices and systems, the concepts of the present invention may be practiced as a number of related methods.

An additional method consistent with the present invention is a method of acquiring a two-dimensional x-ray image of patient anatomy from a desired view direction. The method comprises generating the two-dimensional image using an x-ray imager; specifying a view direction in a three-dimensional image representing the patient anatomy; generating a two-dimensional digitally reconstructed radiograph (DRR) image based on the three-dimensional image and the specified view direction; and determining that the two-dimensional x-ray image corresponds to the desired view direction by matching the DRR image to the x-ray image.

Another method consistent with the present invention is a method of calculating angle between a surgical instrument and a plane selected in an x-ray image. The method comprises a number of steps, including: defining at least two points in the x-ray image; defining a plane passing through the x-ray image as the plane including the two points and linear projections of the two points as dictated by a calibration transformation used to calibrate the x-ray image for its particular imaging device; sensing a position of the surgical instrument in three-dimensional space; and calculating the angle between intersection of a projection of the surgical instrument in three-dimensional space and the plane.

Yet another method consistent with the present invention is a method for aligning a fluoroscopic imager with a view direction of the medial axis of a patient's pedicle. The method comprises displaying a three-dimensional image of an axial cross-section of vertebra ofthe patient; extracting an angle from the three-dimensional image corresponding to the angle separating an anterior/posterior axis and the medial axis of the pedicle; aligning the fluoroscopic imager with a long axis of the patient; and rotating the fluoroscopic imager about the long axis of the patient through the measured angle.

BRIEF DESCRIPTION OF THE DRAWINGS

The accompanying drawings, which are incorporated in and constitute a part of this specification, illustrate several embodiments consistent with this invention and, together with the description, help explain the principles of the invention. In the drawings.

DETAILED DESCRIPTION

As described herein, novel methods and systems improve surgical navigational guidance using one or more fluoroscopic x-ray images. The methods and systems may be used for either navigational guidance using only two-dimensional fluoroscopic images or for navigational guidance using a combination of two-dimensional fluoroscopic images and three-dimensional volumetric images, such as CT or MRI images.

Reference will now be made in detail to embodiments of the invention, examples of which are illustrated in the accompanying drawings. Wherever possible, the same reference number, will be used throughout the drawings to refer to the same or like parts.

System Overview

Figure 1:
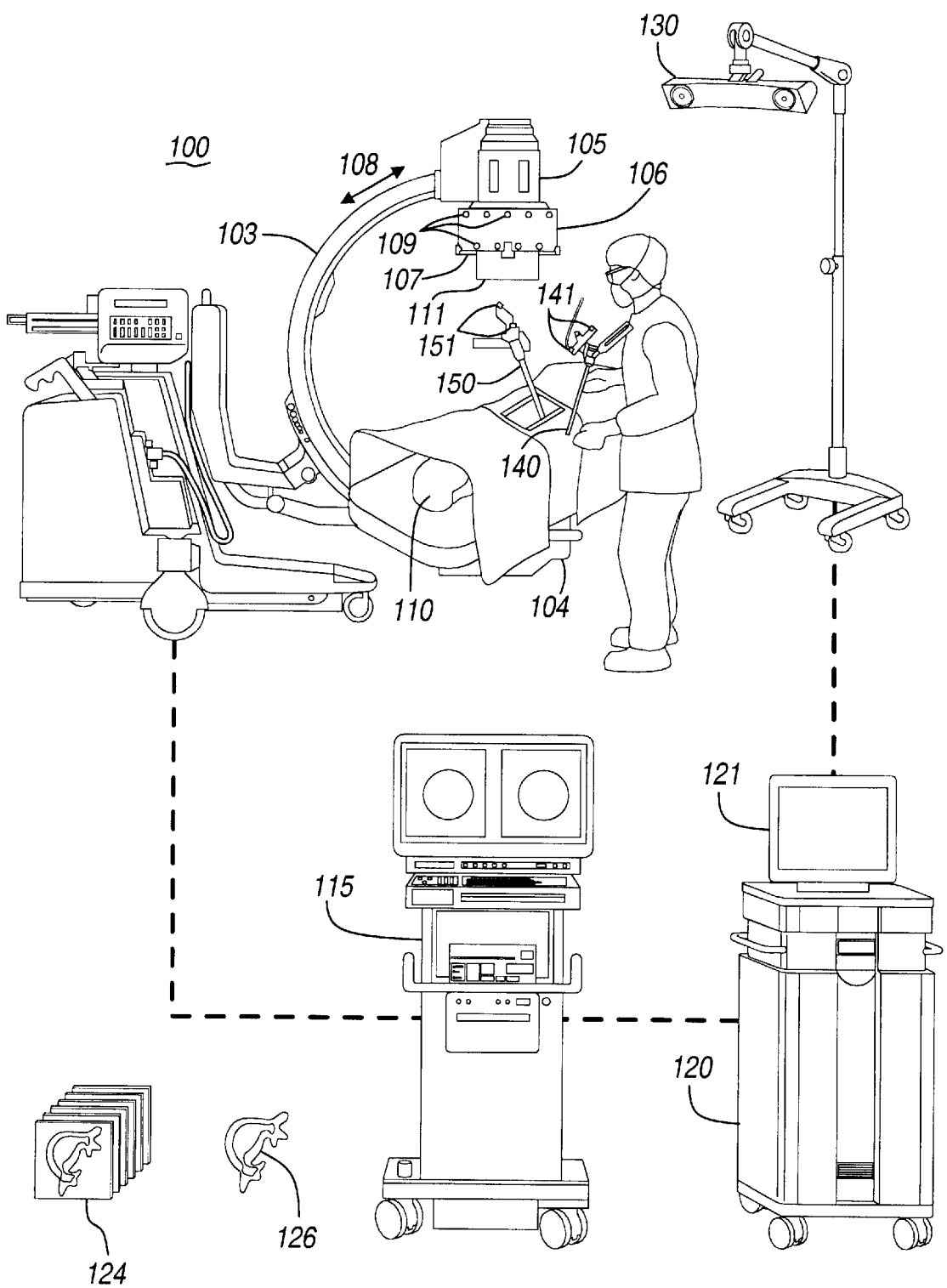
FIG. 1 is a diagram of an exemplary imaging system used to acquire x-ray images.

FIG. 1 is a diagram of an exemplary imaging system used to acquire x-ray images. Fluoroscopic imaging device 100 is a fluoroscopic C-arm x-ray imaging device that includes C-arm 103, x-ray source 104, x-ray receiving section 105, a calibration and tracking target 106, and radiation sensors 107. Calibration and tracking target 106 includes infrared reflectors (or alternatively infrared emitters) 109 and calibration markers 111. C-arm control computer 115 allows a physician to control the operation of imaging device 100, such as setting imaging parameters.

One appropriate implementation of imaging device 100 is the "Series9600 Mobile Digital Imaging System," from OEC Medical Systems, Inc., of Salt Lake City, Utah, although calibration and tracking target 106 and radiation sensors 107 are typically not included in she Series9600 Mobile Digital Imaging System and may have to be added. The "Series9600 Mobile Digital Imaging System" is otherwise structurally similar to imaging system 100.

In operation, x-ray source 104 generates x-rays that propagate through patient 110 and calibration target 106, and into x-ray receiving section 105. Receiving section 105 generates an image representing the intensities of the received x-rays. Typically, receiving section 105 comprises an image intensifier that converts the x-rays to visible light and a charge coupled device (CCD) video camera that converts the visible light to digital images. Receiving section 105 may also be a device that converts x-rays directly to digital images, thus potentially avoiding distortion introduced by first converting to visible light.

Fluoroscopic images taken by imaging device 100 are transmitted to computer 115, where they may further be forwarded to computer 120. Computer 120 provides facilities or displaying (on monitor 121), saving, digitally manipulating, or printing a hard copy of the received images. Three-dimensional images, such as pre-acquired patient specific CT/MR data set 124 or a three-dimensional atlas data set 126 (described in more detail below) may also be manipulated by computer 120 and displayed by monitor 121. Images, instead of or in addition to being displayed on monitor 121, may also be displayed to the physician through a head-up-display.

Although computers 115 and 120 are shown as two separate computers, they alternatively could be variously implemented as multiple computers or as a single computer that performs the functions performed by computers 115 and 120. In this case, the single computer would receive input from both C-arm imager 100 and tracking sensor 130.

Radiation sensors 107 sense the presence of radiation, which is used to determine whether or not imaging device 100 is actively imaging. The result of their detection is transmitted to processing computer 120. Alternatively, a person may manually indicate when device 100 is actively imaging or this function can be built into x-ray source 104, x-ray receiving section 105, or control computer 115.

In operation, the patient is positioned between the x-ray source 104 and the x-ray receiving section 105. In response to an operator's command input at control computer 115, x-rays emanate from source 104 and pass through patient 110, calibration target 106, and into receiving section 105, which generates a two-dimensional image of the patient.

C-arm 103 is capable of rotating relative to patient 110, allowing images of patient 110 to be taken from multiple directions. For example, the physician may rotate C-arm 103 in the direction of arrows 108 or about the long axis of the patient. Each of these directions of movement involves rotation about a mechanical axis of the C-arm. In this example, the long axis of the patient is aligned with the mechanical axis of the C-arm.

Figure 2:
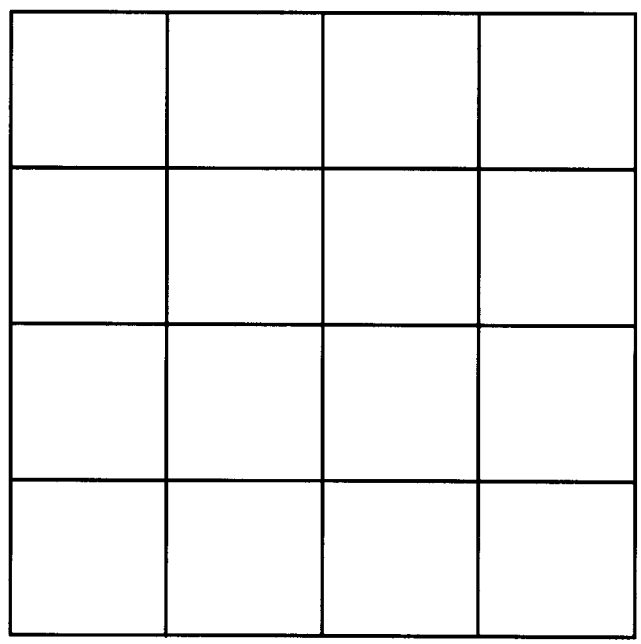
FIG. 2 is an image illustrating true and distorted images.
Figure 2:
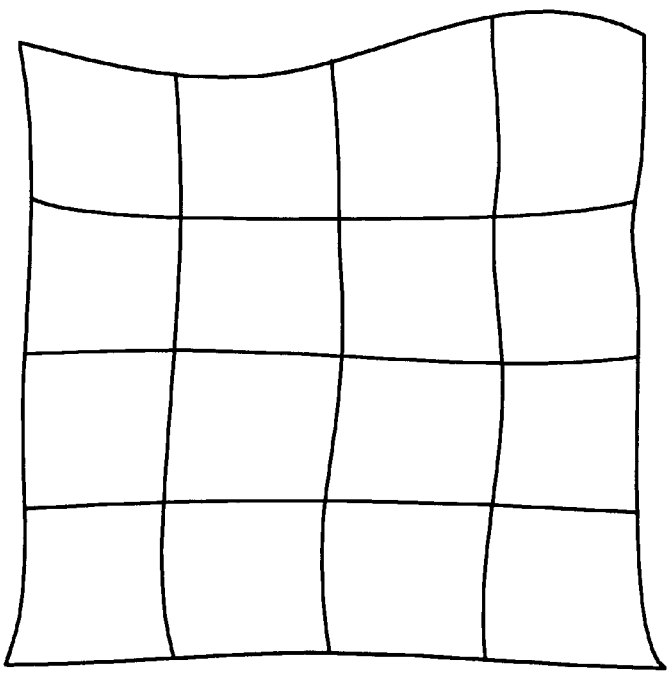

Raw images generated by receiving section 105 tend to suffer from undesirable distortion caused by a number of factors, including inherent image distortion in the image intensifier and external electromagnetic fields. Drawings representing ideal and distorted images are shown in FIG. 2. Checkerboard 202 represents the ideal image of a checkerboard shaped object. The image taken by receiving section 105, however, can suffer significant distortion, as illustrated by distorted image 204.

Figure 3A:
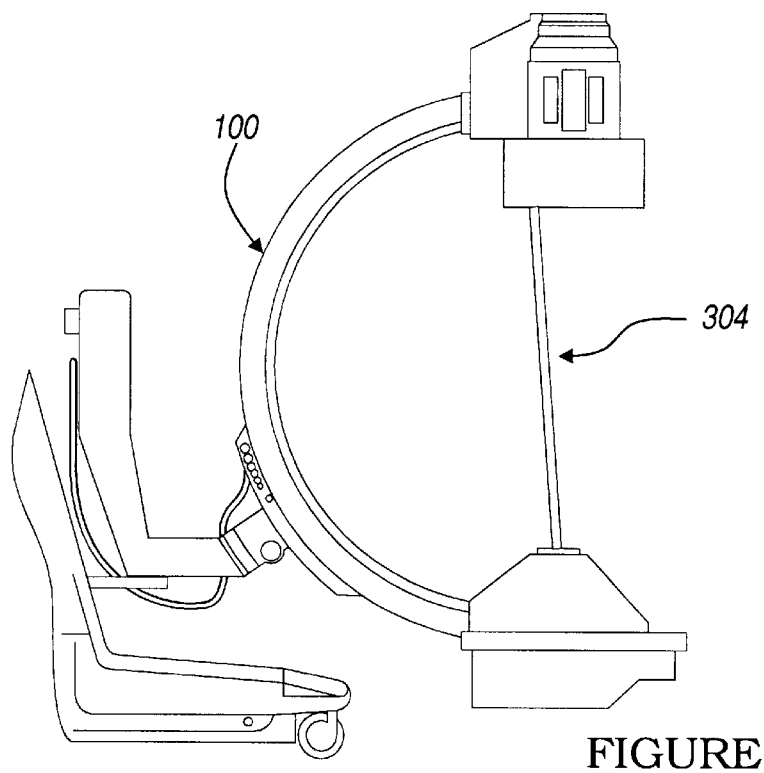
FIGS. 3A and 3B illustrate a projective transformation in a fluoroscopic C-arm imager.
Figure 3B:
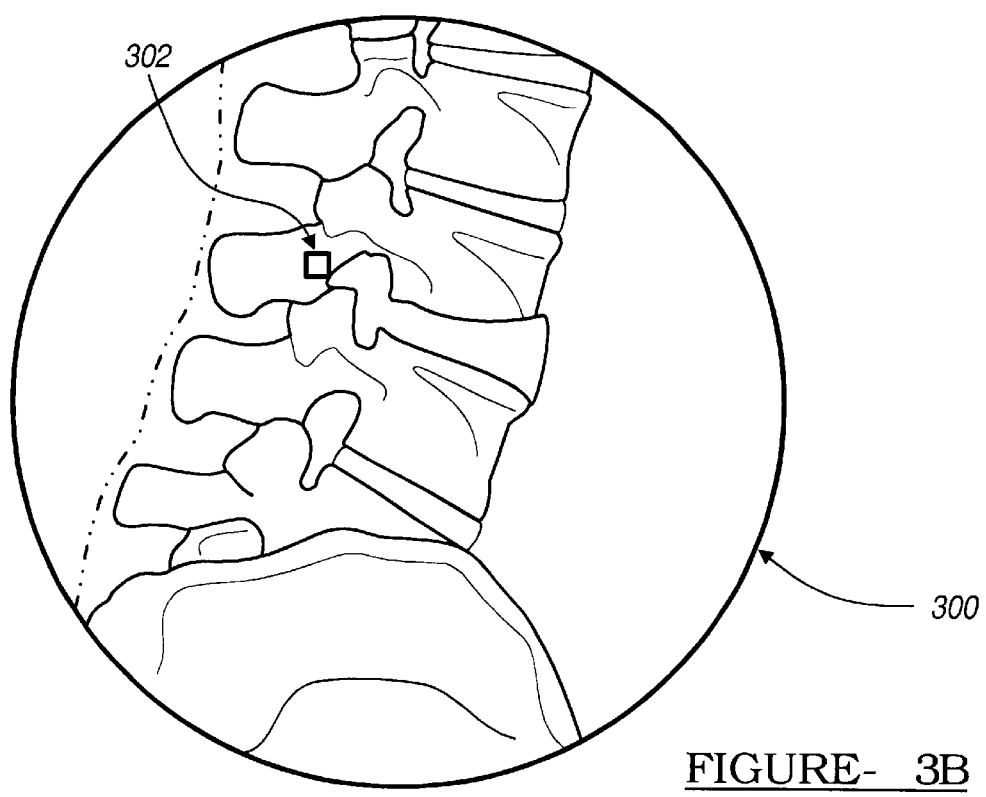

The image formation process in a system such as fluoroscopic C-arm imager 100 is governed by a geometric projective transformation which maps lines in the fluoroscope's field of view to points in the image (i.e., within the x-ray receiving section 105). This concept is illustrated in FIGS. 3A and 3B. Image 300 (and any image generated by the fluoroscope) is composed of discrete picture elements (pixels), an example of which is labeled as 302. Every pixel within image 300 has a corresponding three-dimensional line in the fluoroscope's field of view. For example, the line corresponding to pixel 302 is labeled as 304. The complete mapping between image pixels and corresponding lines governs projection of objects within the field of view into the image. The intensity value at pixel 302 is determined by the densities of the object elements (i.e., portions of a patient's anatomy, operating room table, etc.) intersected by the line 304. For the purposes of computer assisted navigational guidance, it is necessary to estimate the projective transformation which maps lines in the field of view to pixels in the image, and vice versa. Geometric projective transformation is well known in the art.

Intrinsic calibration, which is the process of correcting image distortion in a received image and establishing the projective transformation for that image, involves placing "calibration markers" in the path of the x-ray, where a calibration marker is an object opaque or semi-opaque to x-rays. Calibration markers 111 are rigidly arranged in predetermined patterns in one or more planes in the path of the x-rays and are visible in the recorded images. Tracking targets, such as emitters or reflectors 109, are fixed in a rigid and known position relative to calibration markers 111.

Because the true relative position of the calibration markers 111 in the recorded images are known, computer 120 is able to calculate an amount of distortion at each pixel in the image (where a pixel is a single point in the image). Accordingly, computer 120 can digitally compensate for the distortion in the image and generate a distortion-free, or at least a distortion improved image. Alternatively, distortion may be left in the image, and subsequent operations on the image, such as superimposing an iconic representation of a surgical instrument on image (described in more detail below), may be distorted to match the image distortion determined by the calibration markers. The same calibration markers can also be used to estimate the geometric perspective transformation, since the position of these markers are known with respect to the tracking target emitters or reflectors 109 and ultimately with respect to tracking sensor 130. A more detailed explanation of methods for performing intrinsic calibration is described in the references B. Schuele et al., "Correction of Image Intensifier Distortion for Three-Dimensional Reconstruction," presented at SPIE Medical Imaging 1995, San Diego, Calif., 1995 and G. Champleboux et al., "Accurate Calibration of Cameras and Range Imaging Sensors: the NPBS Method," Proceedings of the 1992 IEEE International Conference on Robotics and Automation, Nice, France, May 1992, and U.S. application Ser. No. 09/106,109, filed on Jun. 29, 1998 by the present assignee, the contents of which are hereby incorporated by reference.

Calibration and tracking target 106 may be attached to x-ray receiving section 105 Of the C-arm. Alternately, the target 106 can be mechanically independent of the C-arm, in which case it should be positioned such that the included calibration markers 111 are visible in each fluoroscopic image to be used in navigational guidance. Element 106 serves two functions. The first, as described above, is holding calibration markers 111 used in intrinsic calibration. The second function, which is described in more detail below, is holding infrared emitters or reflectors 109, which act as a tracking target for tracking sensor 130.

Tracking sensor 130 is a real-time infrared tracking sensor linked to computer 120. Specially constructed surgical instruments and other markers in the field of tracking sensor 130 can be detected and located in three-dimensional space. For example, a surgical instrument 140, such as a drill, is embedded with infrared emitters or reflectors 141 on its handle. Tracking sensor 130 detects the presence and location of infrared emitters or reflectors 141. Because the relative spatial locations of the emitters or reflectors in instrument 140 are known a priori, tracking sensor 130 and computer 120 are able to locate instrument 140 in three-dimensional space using well known mathematical transformations. Instead of using infrared tracking sensor 130 and corresponding infrared emitters or reflectors, other types of positional location devices are known in the art, and may be used. For example, a positional location device may also be based on magnetic fields, sonic emissions, or radio waves.

Reference frame marker 150, like surgical instrument 140, is embedded with infrared emitters or reflectors, labeled 151. As with instrument 140, tracking sensor 130 similarly detects the spatial location of emitters/reflectors 151, through which tracking sensor 130 and computer 120 determine the three-dimensional position of dynamic reference frame marker 150. The determination of the three-dimensional position of an object relative to a patient is known in the art, and is discussed, for example, in the following references, each of which is hereby incorporated by reference: PCT Publication WO 96/11624 to Bucholz et al., published Apr. 25, 1996; U.S. Pat. No. 5,384,454 to Bucholz; U.S. Pat. No. 5,851,183 to Bucholz; and U.S. Pat. No. 5,871,445 to Bucholz.

During an operation, dynamic reference frame marker 150 is attached in a fixed position relative to the portion of the patient to be operated on. For example, when inserting a screw into the spine of patient 110, dynamic reference frame marker 150 may be physically attached to a portion of the spine of the patient. Because dynamic reference frame 150 is in a fixed position relative to the patient anatomy, and instrument 140 can be accurately located in three dimensional space relative to dynamic reference frame 150, instrument 140 can also be located relative to the patient's anatomy.

As discussed above, calibration and tracking target 106 also includes infrared emitters or reflectors 109 similar to those in instrument 140 or dynamic reference frame 150. Accordingly, tracking sensor 130 and computer 120 may determine the three-dimensional position of calibration target 106 relative to instrument 140 and/or dynamic reference frame 150 and thus the patient position.

System Operation

In general, the imaging system shown in FIG. 1 assists physicians performing surgery by displaying real-time or pre-acquired images, such as fluoroscopic x-ray images, of patient 110 on display 121. Representations of surgical instruments 140 are overlaid on pre-acquired fluoroscopic images of patient 110 based on the position of the instruments determined by tracking sensor 130. In this manner, the physician is able to see the location of the instrument relative to the patient's anatomy, without the need to acquire real-time fluoroscopic images, thus greatly reducing radiation exposure to the patient and to the surgical team. "Pre-acquired," as used herein, is not intended to imply any required minimum duration between receipt of the x-ray signals and displaying the corresponding image. Momentarily storing the corresponding digital signal in computer memory while displaying the fluoroscopic image constitutes pre-acquiring the image.

Figure 4:
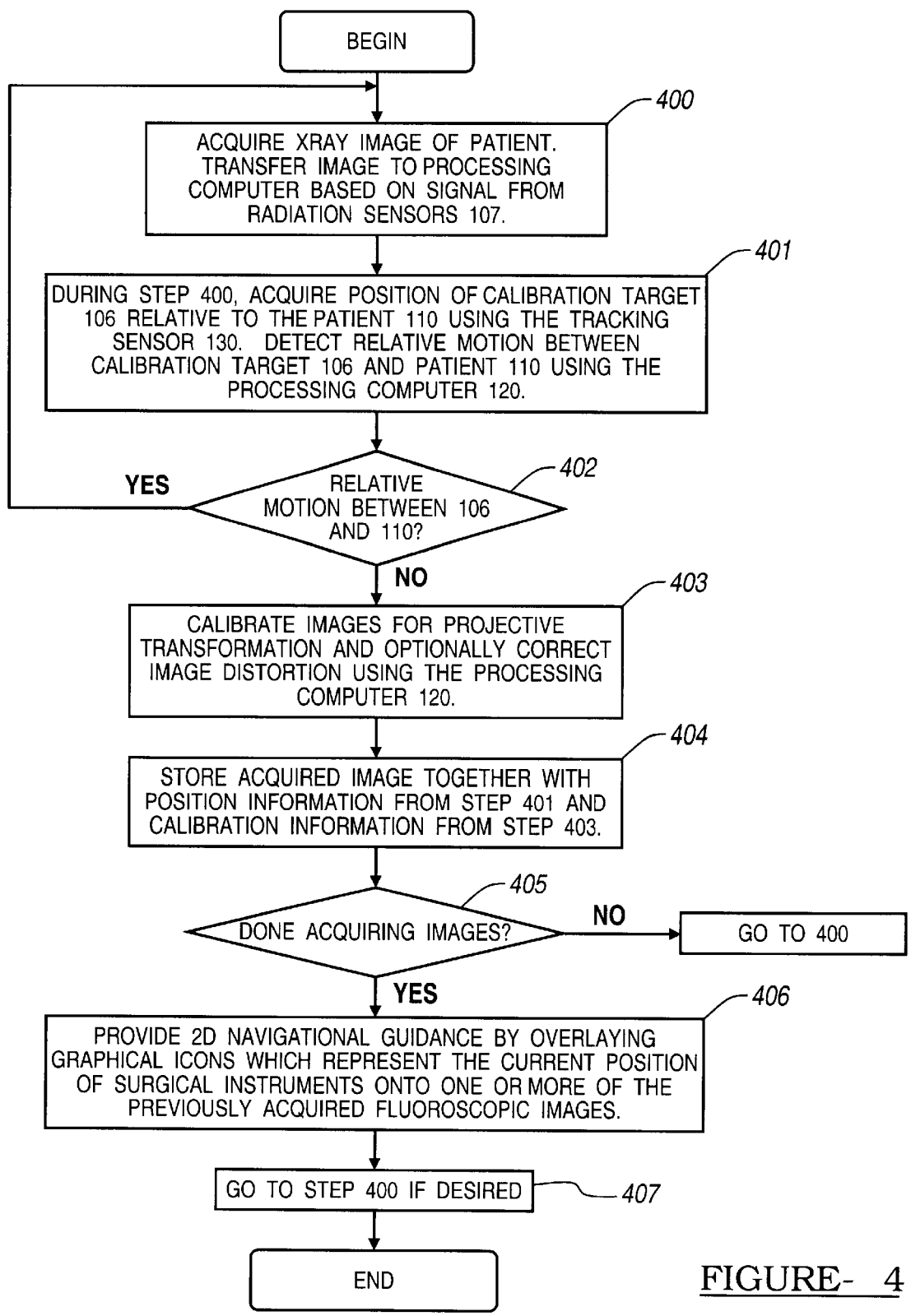
FIG. 4 is a flow chart illustrating methods consistent with the present invention for performing two-dimensional navigational guidance.

FIG. 4 is a flow chart illustrating methods consistent with the present invention for performing two-dimensional navigational guidance using the system of FIG. 1. The physician begins by acquiring one or more fluoroscopic x-ray images of patient 110 using imager 100 (step 400). As previously mentioned, acquiring an x-ray image triggers radiation sensors 107, which informs computer 120 of the beginning and end of the radiation cycle used to generate the image. For a fluoroscopic x-ray image acquired with imager 100 to be useable for navigational guidance, imager 100, when acquiring the image, should be stationary with respect to patient 110. If C-arm 103 or patient 110 is moving during image acquisition, the position of the fluoroscope will not be accurately determined relative to the patient's reference frame. Thus, it is important that the recorded position of imager 100 reflects the true position of the imager at the time of image acquisition. If imager 100 moves during the image acquisition process, or if imager 100 moves after image acquisition but before its position is recorded the calibration will be erroneous, thus resulting in incorrect graphical overlays. To prevent this type of erroneous image, computer 120 may examine the position information from tracking sensor 130 while radiation sensors 107 are signaling radiation detection. If the calibration and tracking target 106 moves relative to dynamic reference frame 150 during image acquisition, this image is marked as erroneous. (Steps 401 and 402).

At the end of the radiation cycle, computer 120 retrieves the acquired image from C-arm control computer 115 and retrieves the location information of target marker 106 and dynamic reference frame 150 from tracking sensor 130. Computer 120 calibrates the acquired image, as described above, to learn its projective transformation and optionally to correct distortion in the image, (step 1403), and then stores the image along with its positional information (step 404). The process of steps 400–404 is repeated for each image that is to be acquired (step 405).

Because the acquired images are stored with the positional information of the calibration and tracking target 106 and dynamic reference frame 150, the position of C-arm 103, x-ray source 104, and receiving section 105 for each image, relative to patient 110, can be computed based upon the projective transformation identified in the calibration process. During surgery, tracking sensor 130 and computer 120 detect the position of instrument 140 relative to dynamic reference frame 150, and hence relative to patient 110. With this information, computer 120 dynamically calculates, in real-time, the projection of instrument 140 into each fluoroscopic image as the instrument is moved by the physician. A graphical representation of instrument 140 may then be overlaid on the fluoroscopic images (step 406). The graphical representation of instrument 140 is an iconic representation of where the actual surgical instrument would appear within the acquired fluoroscopic x-ray image if imager 100 was continuously acquiring new images from the same view as the original image. There is no theoretical limit to the number of fluoroscopic images on which the graphical representations of instrument 140 may be simultaneously overlaid.

Figure 5A:
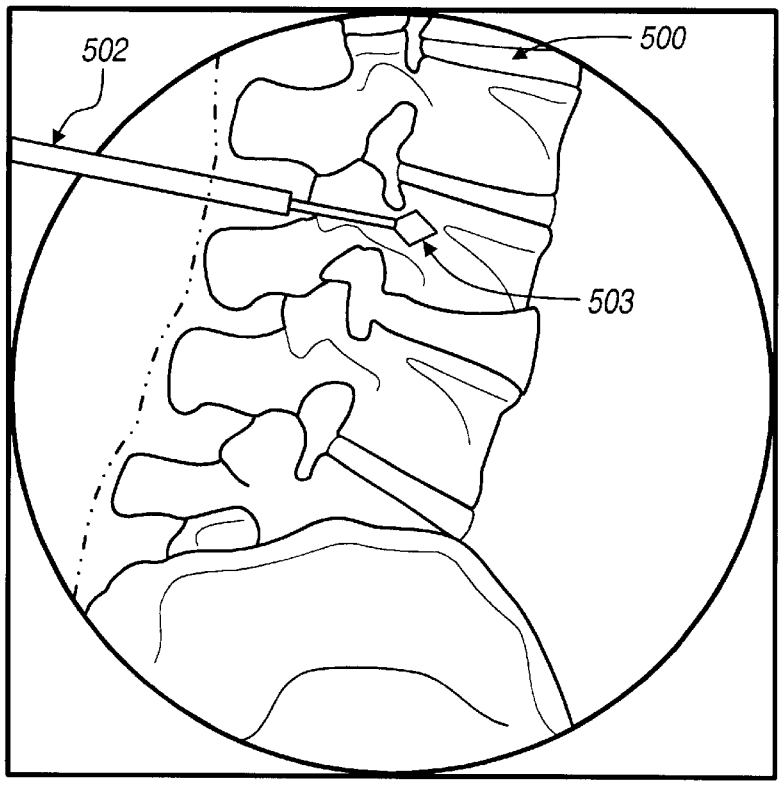
FIGS. 5A and 5B are exemplary fluoroscopic x-ray images illustrating the iconic graphical overlay of a surgical instrument.
Figure 5B:
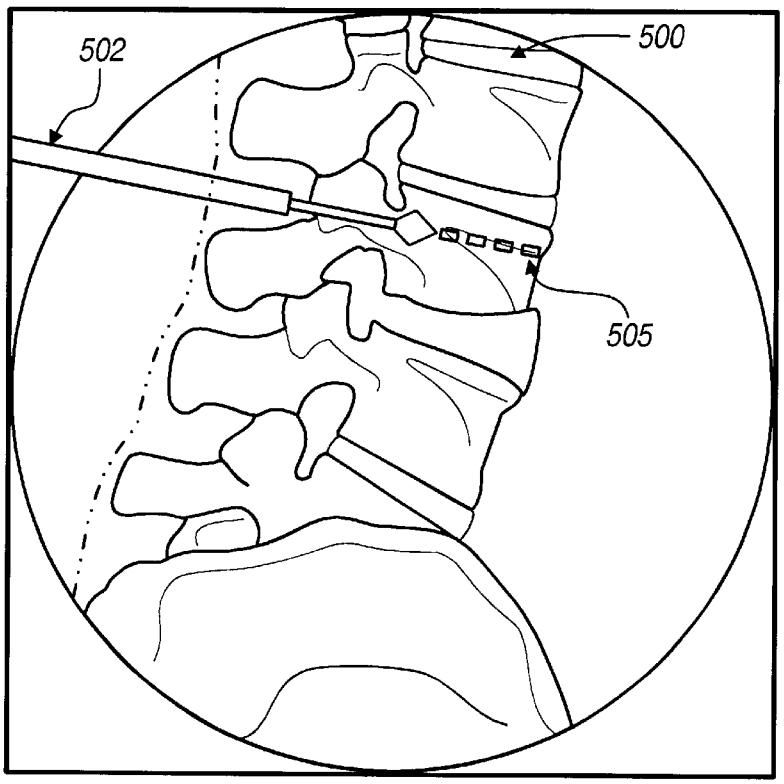

FIGS. 5A and 5B are exemplary fluoroscopic x-ray images illustrating the iconic graphical overlay of a surgical instrument. Fluoroscopic image 500, shown in FIG. 5A, is an image of a lateral view of the lumbar spine. Graphical overlay 502 is the iconic overlay of a surgical instrument, such as a drill, within image 500. As the physician moves the drill, computer 120 recalculates and displays the new location of graphical overlay 502. The diamond shaped end of overlay 502, labeled as area 503, represents the tip of the instrument. The physician can use image 500 and overlay 502 to visualize the position and orientation of the surgical tool relative to the patient's anatomy.

In certain situations, the physician may wish to know where the tip of the instrument would be if the instrument were projected along a line given by the instrument's current trajectory. Consistent with an aspect of the present invention, at the physician's command, computer 120 may calculate and display this projection. Area 505 in FIG. 5B is a projection of graphical overlay 502. As shown, the "look-ahead" trajectory 505 of overlay 502 is displayed in a different line style than overlay 502. Computer 120 may vary the length of look-ahead trajectory 505 as directed by the physician through a suitable computer interface device, such as a keypad, mouse, or touch pad. In this manner, computer 120 assists the physician in visualizing where the instrument would be in the patient if it were advanced a predetermined distance in the patient.

Although the "look-ahead" technique described above projected the graphical representation of the instrument into the image, there is no requirement that the instrument's graphical representation be in the space of the image for look-ahead trajectory 505 to be projected into the image. For example, the physician may be holding the instrument above the patient and outside the space of the image, so that the representation of the instrument does not appear in the image. However, it may still be desirable to project look-ahead portion 505 into the image to facilitate planning of a surgical procedure.

When surgical instrument 140 is perpendicular to the plane of the fluoroscopic image, the graphical overlay of the surgical instrument essentially collapses to a point, making it difficult to view. To alleviate this problem, computer 120 may optionally use a different graphical representation of instrument 140 when the distance in the image plane between the tip and the tail of instrument 140 becomes smaller than a fixed distance (e.g., 15 pixels).

Figure 6:
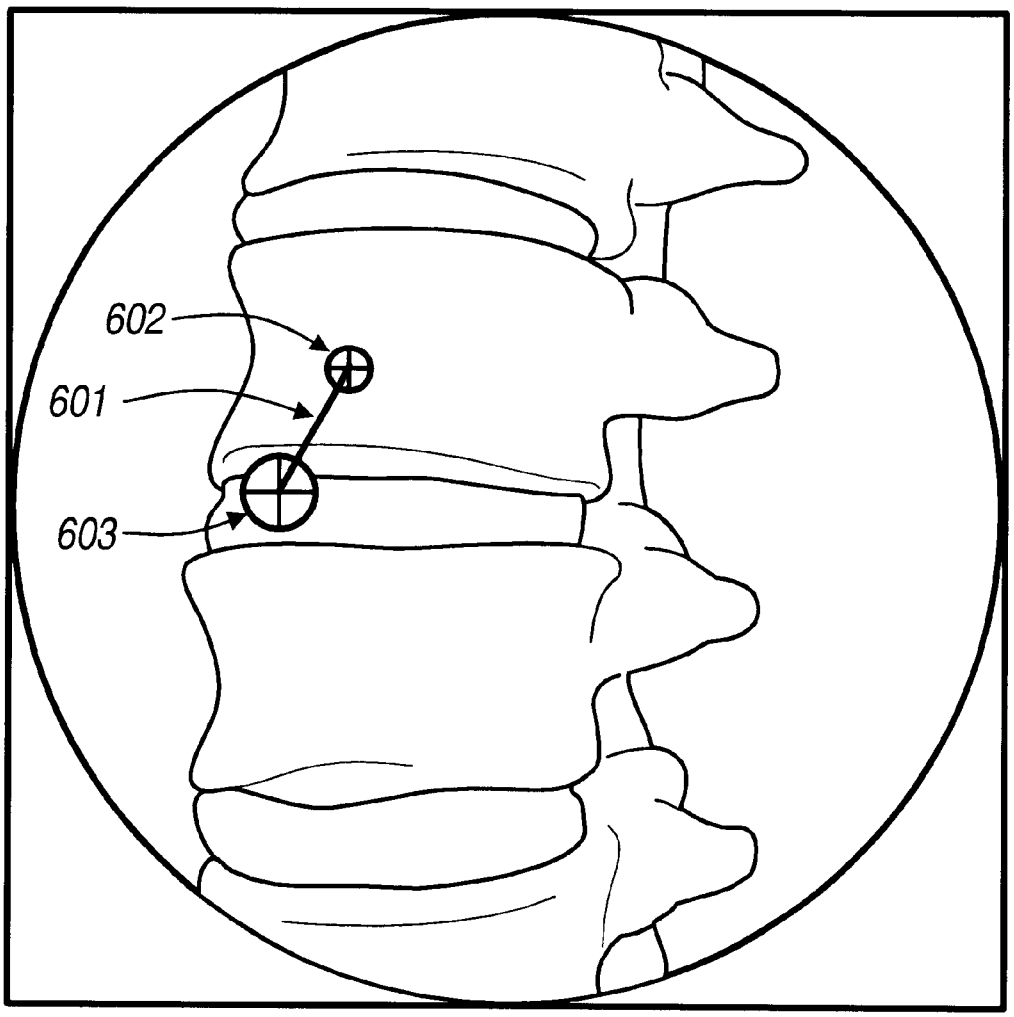
FIG. 6 is a fluoroscopic image including a "cross hair" graphical overlay of an instrument.

FIG. 6 is a fluoroscopic image including graphical overlay 601 of instrument 140, including a small "cross hair image" representing tip 602 and a larger cross hair representing tail 603 of instrument 601. Computer 120 automatically switches between the cross hair representation shown in FIG. 6 and the "straight line" representation shown in FIG. 5.

Frequently, the physician would like to acquire two complementary fluoroscopic images of the patient, such as images from an anterior/posterior view and a lateral view of the vetebral discs. The complementary views are related to one another by a rotation about an axis by a particular amount. For example, an anterior/posterior view is related to a lateral view by a 90 degree rotation around the axis running parallel through the length of the patient. When the mechanical axis of rotation of C-arm 103 is aligned with the axis relating the complementary views (e.g., when the mechanical axis is aligned with the axis running through the length of the patient), the physician can accurately and quickly switch between the complementary views by simply rotating C-arm 103 through the separation of the complementary views (usually 90 degrees). Generally, however, the axis of rotation of C-arm 103 is not inherently aligned with the axis that relates the complementary views, requiring the physician to perform a series of time consuming trial-and-error based adjustments of the fluoroscope's position through two or more axes of rotation.

Consistent with an aspect of the present invention, software on computer 120 allows the surgeon to easily adjust the fluoroscope's position so that one of its mechanical rotation axes, such as the axis of rotation shown by arrows 108 in FIG. 1, is aligned with the axis of rotation relating the complementary views. The surgeon may then acquire the second image in the complementary image set simply by rotating C-arm 103 a certain amount, typically 90 degrees, about the aligned axis.

Figure 7A:
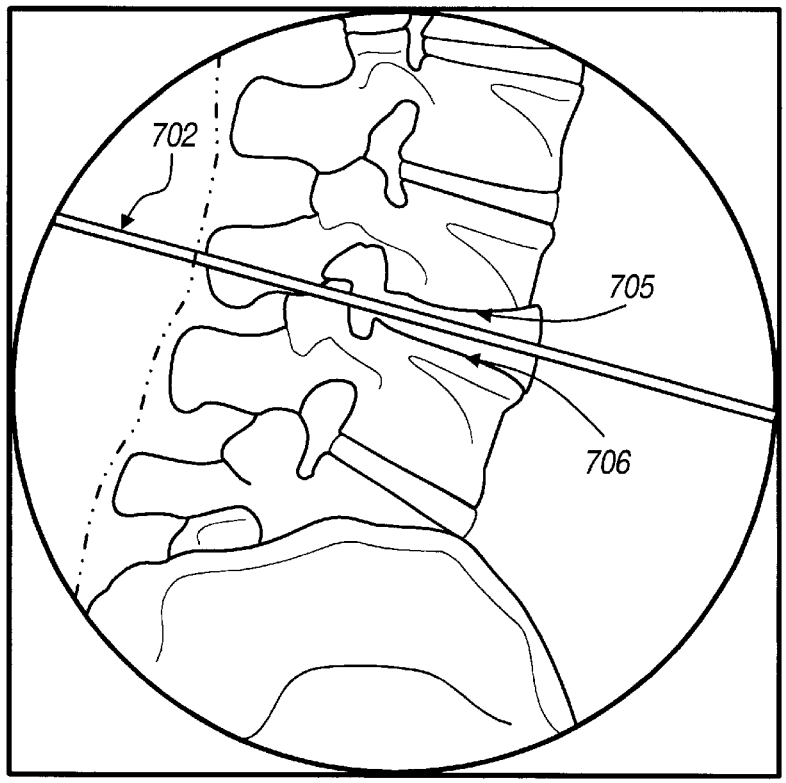
FIGS. 7A–7C illustrate images of complementary views and an axis that relates them.
Figure 7B:
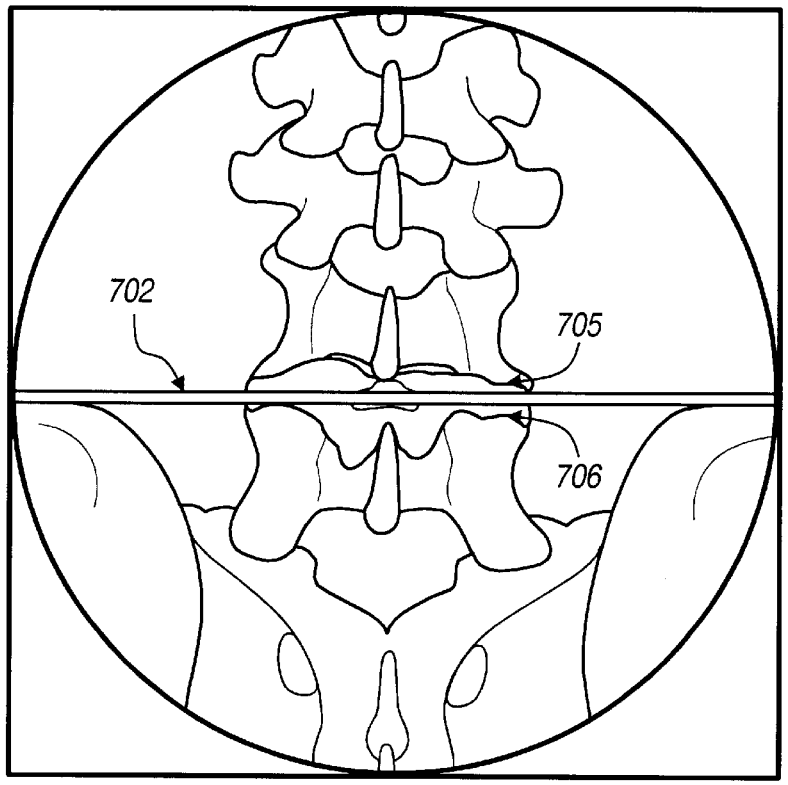
Figure 7C:
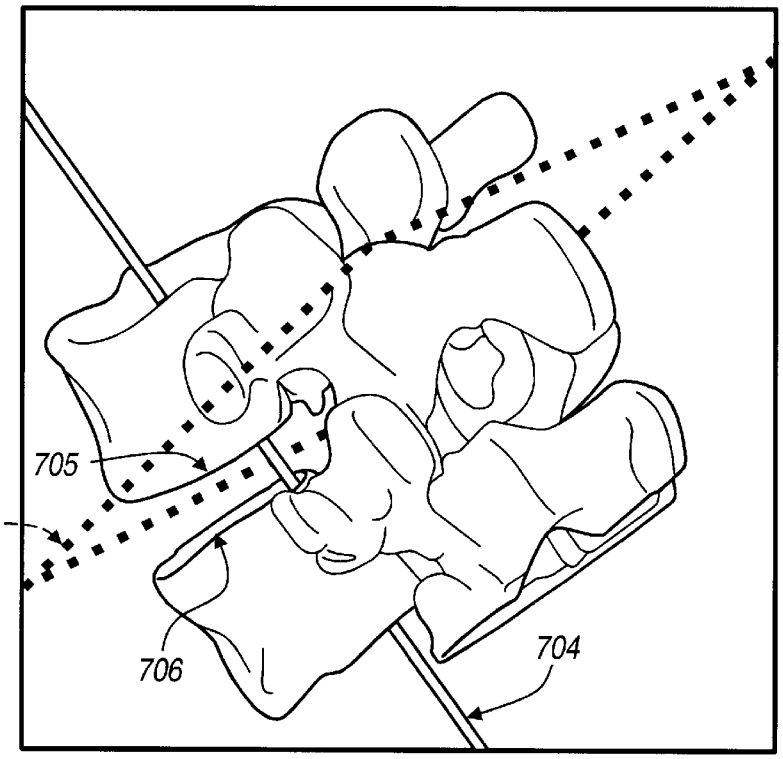

Images of complementary views and the axis that relates them are illustrated in FIGS. 7A–7C. The image of FIG. 7A illustrates a lateral view of the patient's vertebral disc, in which the view direction (i.e., the direction of the central ray of fluoroscopic imager 100) is approximately parallel to the two vertebral end plates, labeled as endplate 705 and endplate 706. Line 702 is the projection of the plane substantially parallel to end plates 705 and 706. Similarly, the image shown in FIG. 7B is an anterior/posterior view of the patient's vertebral disc, in which the view direction is parallel to plane 702. The axis of rotation 704 that spatially relates the image view of FIG. 7A and the image view of FIG. 7B is a line perpendicular to plane 702. That is, rotating the image view of FIG. 7A ninety degrees about the line perpendicular to plane 702 will result in the image view shown in FIG. 7B. FIG. 7C is a three-dimensional representation of the anatomy shown in FIGS. 7A and 7B. The line perpendicular to plane 702 is shown by axis of rotation 704.

Figure 8:
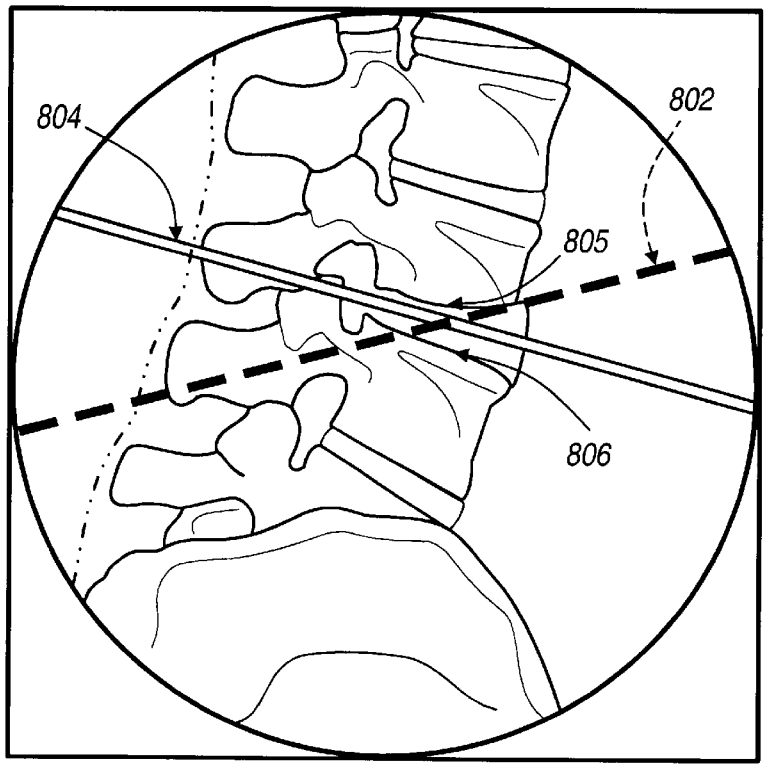
FIG. 8 is an image of a lateral view of a patient's vertebral disc.

FIG. 8 is an image of a lateral view of the patient's vertebral disc, similar to FIG. 7A. In FIG. 8, however, computer 120 has drawn line 802, which represents the projection of a plane that is perpendicular to one of the C-arm's mechanical axes. Line 804 represents the plant, that spatially relates the complementary views. With line 802 visible, the physician may adjust the position of fluoroscopic imager 100 so that line 802 is lined up with line 804. At this point, switching between the complementary views simply involves rotating C-arm 103 about a single mechanical axis.

Although the alignment of lines 802 and 804, as discussed above, was illustrated using both lines 802 and 804 drawn on the fluoroscopic image, in practice, it may only be necessary to display line 802 in the image. In this case, line 804 is mentally visualized by the physician. Additionally, although the relation of complimentary views was discussed using the example of the spine, complimentary fluoroscopic images of other anatomical regions, such as, for example, the pelvis, femur, or cranium, may similarly be obtained by application of the above discussed concepts.

Before, or during, surgery, the physician may find it desirable to input an operation "plan" to computer 120. The plan may, for example, specify a desired trajectory of a surgical instrument superimposed on a fluoroscopic image. During the surgical navigation process, the goal of the surgeon would be to align the graphical icon representing the real-time location of the surgical instrument with the graphical overlay representing the planned trajectory.

Figure 9:
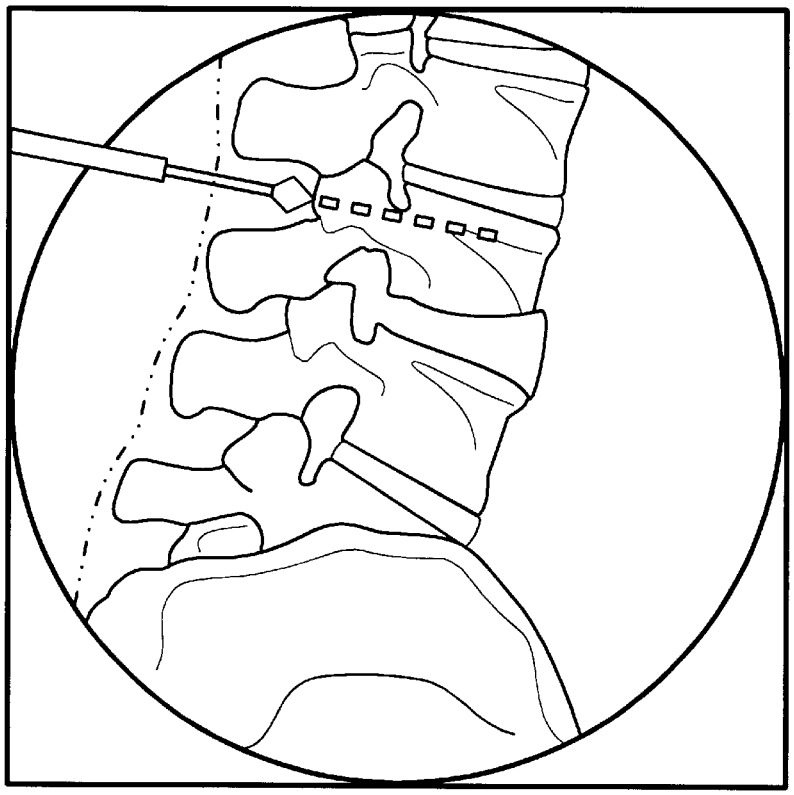
FIG. 9 is an image of a lateral view of a spinal vertebra.

FIG. 9 is an image of a lateral view of a spinal vertebra. Assume the goal of the operation plan is to define a line that passes along a desired trajectory within the image of the vertebra. One method of accomplishing this goal is to directly input the desired trajectory information to computer 120 using traditional computer input devices. While this method of directly interacting with computer 120 is possible, it can be cumbersome and disruptive during surgery. Consistent with an aspect of the present invention, an alternative method of accomplishing this is for the physician to position the surgical instrument on the surface of the bone or skin in the desired orientation, and then project the tip of the instrument forward using the previously described look-ahead technique. More specifically, the desired trajectory is specified by (1) adjusting the position and orientation of the instrument near the patient with virtual look-ahead active, and (2) adjusting the length of the virtual look-ahead. FIG. 9 illustrates the iconic representation of instrument 901 and the virtual look-ahead projection of the instrument 902. Once the desired trajectory is achieved, the surgeon may direct computer 120 to "freeze" the planned trajectory on display 121. The desired trajectory can be obtained using one or more C-arm fluoroscopic images with two or more being required to define a specific three-dimensional trajectory which can then be displayed on any C-arm fluoroscopic view. The freeze operation may be input to computer 120 through, for example, a simple input device such as a foot pedal. The physician may then proceed with the operation, using the overlay of the planned target as a guide.

Figure 10:
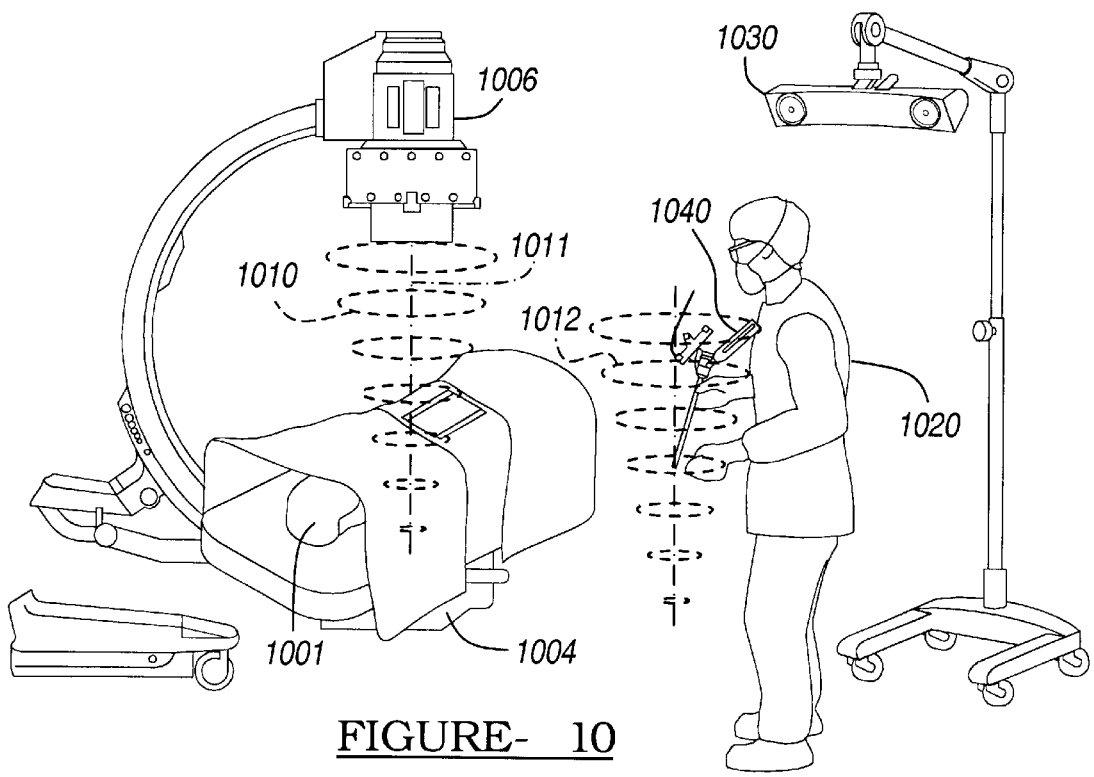
FIG. 10 is a diagram illustrating a system for specifying a planned trajectory of a surgical instrument.

Yet another method consistent with the present invention for specifying a planned trajectory of a surgical instrument, which, unlike the method discussed above, does not require positioning the surgical instrument on or near the patient's bone, is illustrated in FIGS. 10 and As shown in FIG. 10, during the acquisition of an image, patient 1001 is positioned between C-arm x-ray source 1004 and x-ray receiving section 1006. Fluoroscopic images of patient 1001 are created by the x-rays emitted from x-ray source 1004 as they travel in the path generally outlined by cone 1010 through patient 1001. Line 1011, in the center of cone 1010, corresponds to the origin (i.e., the center point) in the acquired fluoroscopic images. Physician 1020, standing within the range of tracking sensor 1030, but away from patient 1001, commands the computer to create an explicit correspondence between the fluoroscope's imaging cone 1010 and a "virtual" cone 1012 at an arbitrary position in space (which is visible to the tracking sensor). Once this virtual cone has been defined, the surgical instrument 1040 can be projected from this virtual cone into one or more pre-acquired fluoroscopic images the same manner as if the instrument were located in the actual cone 1010 corresponding to a given image. In this manner, physician 1020 can plan the trajectory of surgical instrument 1040 by simply moving the instrument in the coordinate system established by the virtual cone.

To define the correspondence between actual and virtual cones, it is necessary for the physician to define the position of the virtual cone relative to the tracking sensor. In general, there are many ways to define a cone in space. For example, the position and orientation of a cone can be defined by three points, one corresponding to its apex, one corresponding to a second point along its central axis, and a third corresponding to the rotation of the cone about the central axis. Therefore, one way to define the cone would be to use the tip of the surgical instrument to define these three points in space relative to the tracking sensor. Another way to define this correspondence is to use a single measurement of a surgical instrument. Using this method, the axis of the instrument corresponds to the axis of the cone, the tip of the instrument corresponds to a fixed point along the axis of the cone (which could be the apex, but could also be another point along the central axis), and the orientation of the instrument about its axis corresponds to the orientation of the cone about its axis. In general any set of measurements which define the position and orientation of a given cone can be used to establish the correspondence between the actual and virtual cones.

Figure 11:
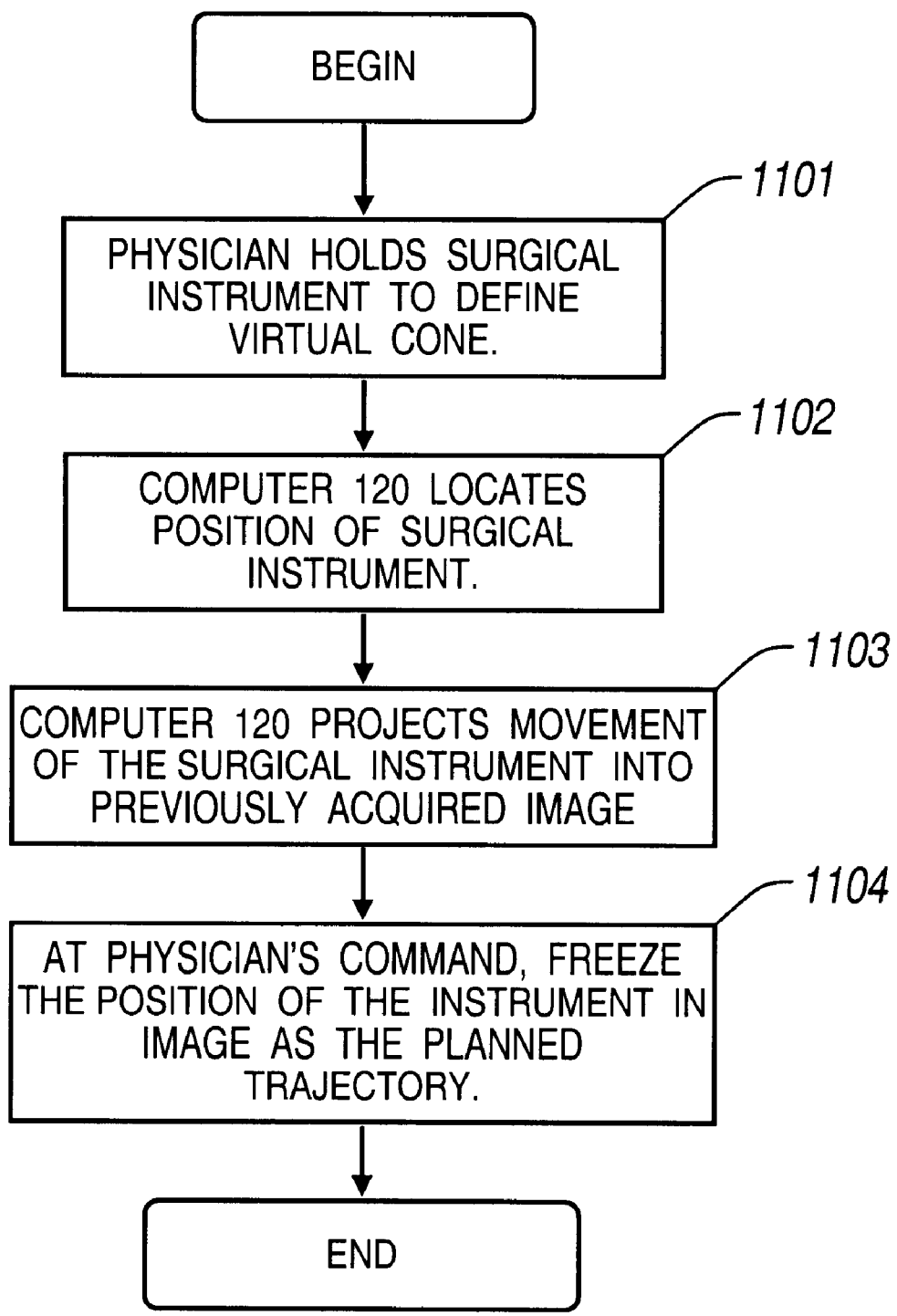
FIG. 11 is a flow chart illustrating a method for specifying a planned trajectory of surgical instrument.

The operations illustrated in FIG. 10 are shown in the flowchart of FIG. 11. To begin, the physician holds the surgical instrument 1040 in the position that defines the virtual cone in the manner as outlined in the previous paragraph (step 1101). Computer 120 locates the position of instrument 1040, which effectively corresponds the position and orientation of the virtual cone to the actual cone (step 1102). Computer 120 projects additional movements of instrument 1040 into one or more previously acquired fluoroscopic images as if the instrument were being moved in the actual cone corresponding to a given image (step 1103). In this manner, the physician can align the instrument to particular points or trajectories within previously acquired images. At the physician's command, computer 120 "freezes" the position and/or orientation of the instrument in the displayed fluoroscopic image(s) and uses those for subsequent processing and plan generation (step 1104).

It is also consistent with this invention to provide automated planning using computer analysis techniques to define an "optimal" trajectory in the C-arm images. Once the optimal trajectory is determined, computer 120 overlays the optimal trajectory in the fluoroscopic image. For example, automated plans can be generated using computational techniques to reduce a specified amount of lordosis in spine surgery.

Alignment of Bone Fragments

Figure 12A:
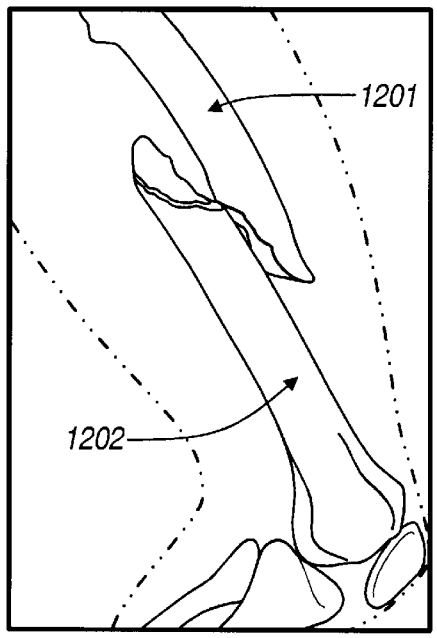
FIGS. 12A through 12C are images of a fracture of a femur containing two bone fragments.

A common clinical problem, especially in orthopaedic trauma, is the realignment (reduction) of broken or misaligned bone fragments. FIG. 12A is a fluoroscopic image of a fracture of the femur containing two bone fragments 1201 and 1202. The physician's job is to realign the bone fragments so that the femur can properly heal.

Figure 13:
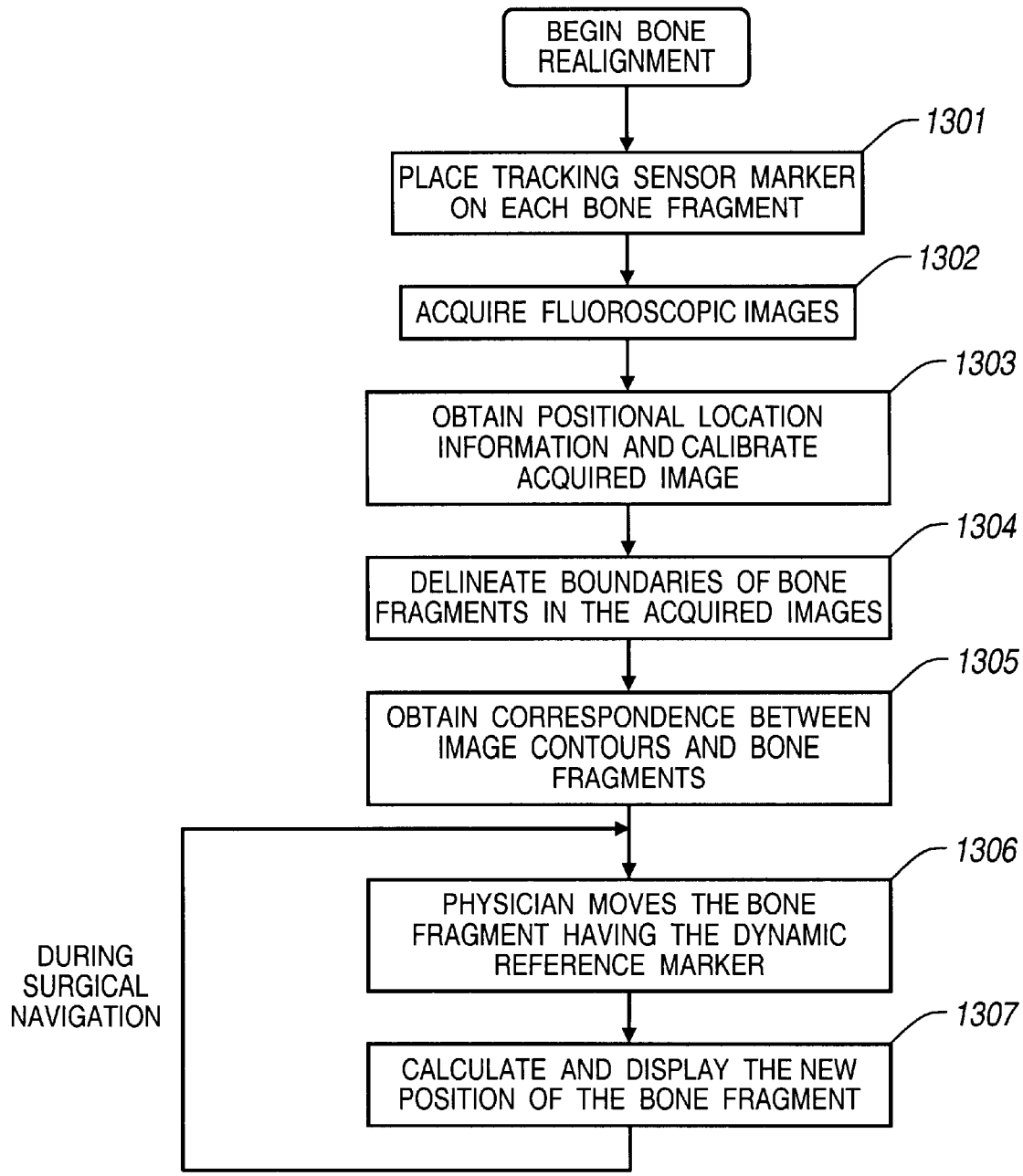
FIG. 13 is a flow chart illustrating methods for aligning bone fragments consistent with the present invention.

FIG. 13 is a flow chart illustrating methods for aligning bone fragments consistent with the present invention. In general, one of bone fragments 1201 or 1202 is used as a fixed reference frame and the other as a dynamic reference frame. When the physician moves the bone fragment corresponding to the dynamic reference frame, tracking sensor 130 detects the movement and updates the x-ray image to reflect the new location of the bone fragment it the patient.

To begin the alignment procedure, the physician places a tracking sensor marker on each of bone fragments 1201 and 1202 (step 1301) and acquires the fluoroscopic images, (step 1302), such as the image shown in FIG. 12A. Computer 120 processes the acquired image to obtain positional location information and to calibrate the image (step 1303, this step is identical to steps 401–403 in FIG. 4).

Figure 12B:
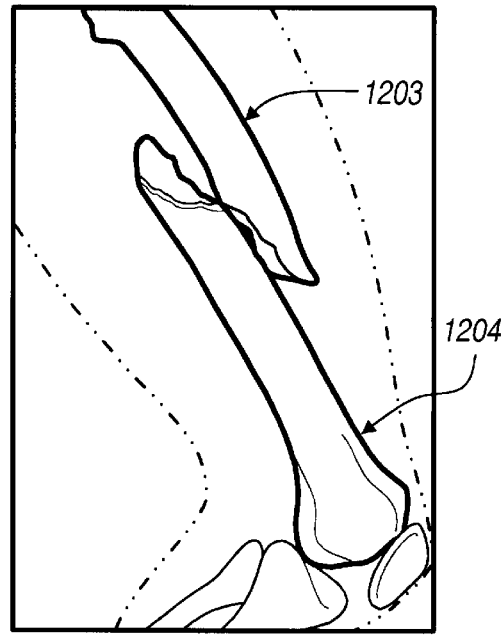

After acquisition of the fluoroscopic image(s), computer 120 uses image detection and extraction techniques to delineate the boundaries of the bone fragments in the images (step 1304). Suitable edge detection algorithms for generating the contours are well known in the art, and may be, for example, the Canny edge detector, the Shen-Casten edge detector, or the Sobel edge detector. An edge detected version of FIG. 12A is shown in FIG. 12B, in which the resulting contour corresponding to bone fragment 1201 is labeled as 1203 and the contour corresponding to bone fragment 1202 is labeled as 1204. Contours 1203 and 1204 may be, as shown in FIG. 12B, graphically superimposed by computer 120 on the acquired image(s).

Overlaying the detected image contours on the fluoroscopic image allows the physcian to easily identify the correspondence between image contours 1203–1204 and bone fragments 1201–1202. The physician inputs this correspondence into computer 120 (step 1305). Alternatively, computer 120 may automatically identify the correspondence between the image contours and the bone fragments. Once the correspondence is established, the physician specifies which contour is to remain fixed and which is to be repositioned. The tracking sensor marker attached to the fragment to be repositioned is referred to as the dynamic reference marker and the tracking sensor marker attached to the fixed fragment is referred to as the fixed reference frame marker, although physically the dynamic reference marker and the fixed reference frame marker may be identical.

Figure 12C:
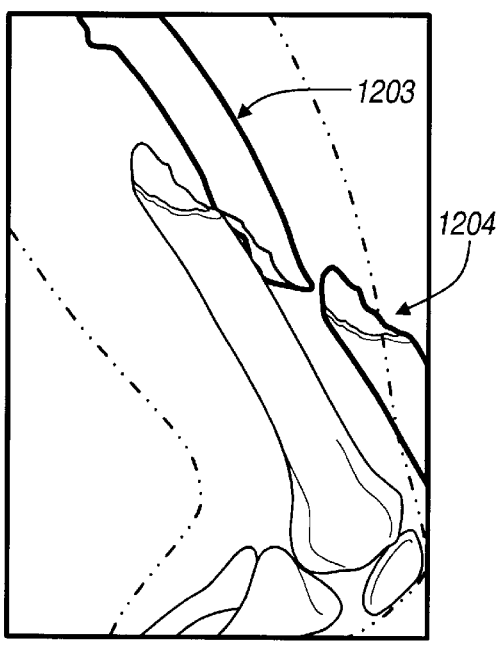

During surgical navigation, the physician moves the bone fragment having the dynamic reference marker (step 1306). Tracking sensor 130 detects the position of the dynamic reference frame marker and the fixed frame marker. With this information and the previously generated positional location information, computer 120 calculates and displays the new position of the dynamic reference frame, and hence its corresponding bone fragment, in the fluoroscopic image (step 1307). FIG. 12C illustrates an updated version of the fluoroscopic image contour 1203 corresponding to the fixed bone fragment and contour 1204 corresponding to the new location of the dynamic reference marker and its bone fragment.

Methods described above for aligning bone fragments may also be applied to the proper alignment of multiple vertebral bodies, for example in the reduction of scoliosis.

Three-Dimensional Images

The navigational guidance system consistent with the present invention is not limited to providing surgical navigational guidance with two-dimensional fluoroscopic images. Three-dimensional volumetric data sets may also be overlaid with graphical representations of a surgical instrument. Three-dimensional data sets (such as CT or MRI) may be either pre-acquired or acquired during the operation.

Two types of three-dimensional data sets are typically used in surgical navigation: patient-specific image data and non-patient specific or atlas data. Patient-specific three-dimensional images are typically acquired prior to surgery using computed tomography (CT), magnetic resonance (MR), or other known three-dimensional imaging modalities, although intra-operative acquisition is also possible. Atlas data is non-patient specific three-dimensional data describing a "generic" patient. Atlas data may be acquired using CT, MR or other imaging modalities from a particular patient; and may even comprise images from several modalities which are spatially registered (e.g., CT and MR together in a common coordinate system). Atlas data may be annotated with supplemental information describing anatomy, physiology, pathology, or "optimal" planning information (for example screw placements, lordosis angles, scoliotic correction plans, etc).

A three-dimensional patient CT or MR data set is shown in FIG. 1 as data set 124 and atlas data is illustrated in FIG. 1 as data set 126.

Before overlaying a three-dimensional image with graphical representations of surgical instruments, the correspondence between points in the three-dimensional image and point in the patient's reference frame must be determined. This procedure is known as registration of the image. One method for performing image registration is described in the previously mentioned publications to Bucholz. Three-dimensional patient specific images can be registered to a patient on the operating room table (surgical space) using multiple two-dimensional image projections. This process, which is often referred to as 2D/3D registration, uses two spatial transformations that can be established. The first transformation is between the acquired fluoroscopic images and the three-dimensional image data set (e.g., CT or MR) corresponding to the same patient. The second transformation is between the coordinate system of the fluoroscopic images and an externally measurable reference system attached to the fluoroscopic imager. Once these transformations have been established, it is possible to directly relate surgical space to three-dimensional image space.

When performing three-dimensional registration, as with two-dimensional registration, imager 100, when acquiring the image, should be stationary with respect to patient 110. If C-arm 103 or patient 110 is moving during image acquisition, the position of the fluoroscope will not be accurately determined relative to the patient's reference frame. Accordingly, the previously described technique for detecting movement of imager 100 during the image acquisition process can be used when acquiring fluoroscopic images that are to be used in 2D/3D registration. That is, as described, computer 120 may examine the position information from tracking sensor 130 while radiation sensors 107 are signaling radiation detection. If the calibration and tracking target 106 moves relative to dynamic reference frame 150 during image acquisition, this image is marked as erroneous.

It may be necessary to acquire complementary fluoroscopic views (e.g., lateral and anterior/posterior) to facilitate 2D/3D registration. The techniques previously discussed in reference to FIGS. 7–8 and relating to the acquisition of complementary views can be applied here.

Once registered, computer 120 may use positional information of instrument 140 to overlay graphical representations of the instrument in the three-dimensional image as well as the two-dimensional fluoroscopic images.

Hybrid Use of Three-Dimensional and Two-Dimensional Image Data

The two-dimensional images generated by imager 100 are not always able to adequately represent the patient's bone structure. For example, fluoroscopic x-ray images are not effective when taken through the length of the patient (i.e., from the point of view looking down at the patient's head or up from the patient's feet) because the large number of bones that the x-rays pass through occlude one another in the final image. However, information required for planning a surgical procedure which is not otherwise available based on two-dimensional image data alone may be extracted from a three-dimensional image data set such as a CT or MR image data set. The extracted information may then be transferred to the two-dimensional x-ray images generated by imager 100 and used in surgical navigation. The following examples describe additional methods for using three-dimensional and two-dimensional data in surgical navigation.

EXAMPLE 1

Figure 14A:
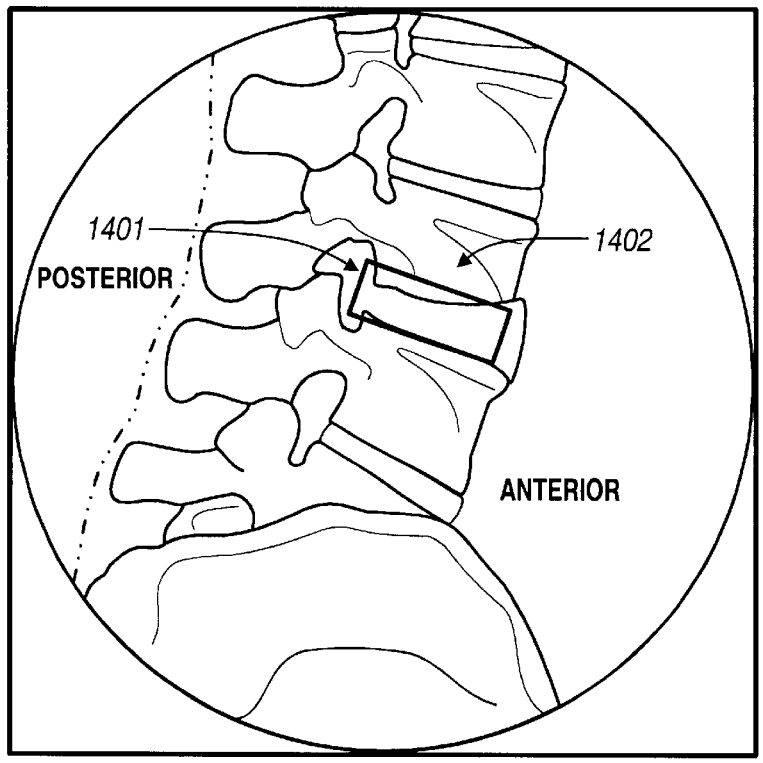
FIGS. 14A and 14B are images illustrating implantation of an inter-vertebral cage in the spine of a patient.
Figure 14B:
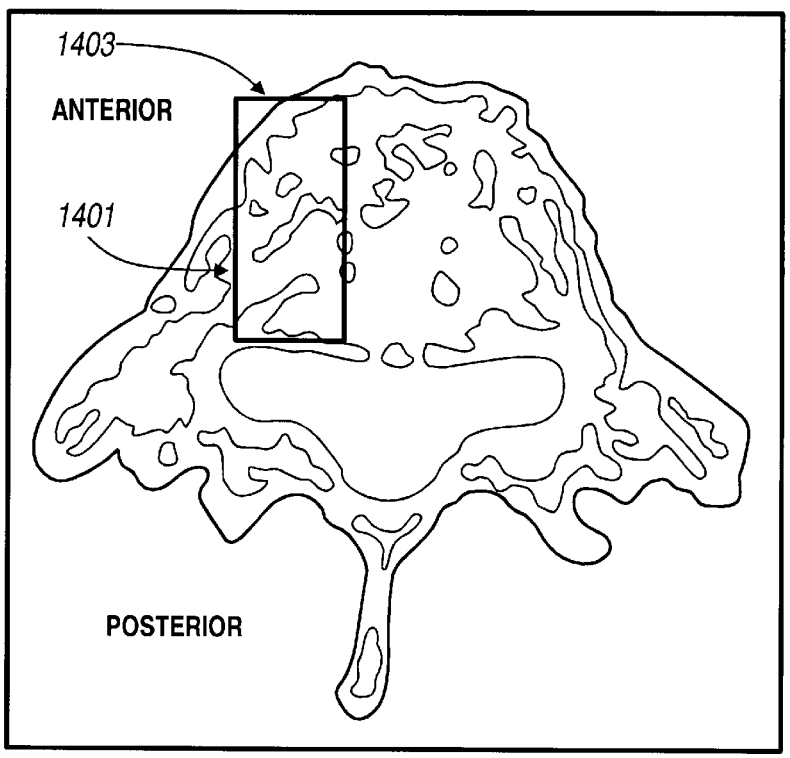

Importing Three-Dimensional Surgical Implant Specifications to Two-Dimensional Images FIGS. 14A and 14B are images illustrating the implantation of an inter-vertebral cage in the spine of a patient. An inter-vertebral cage is a roughly cylindrical spinal implant that is inserted in the disc space between adjacent spinal vertebrae. The physician may find it difficult, if not impossible, to choose the appropriate length of an inter-vertebral cage based upon two-dimensional images such as the image of FIG. 14A.

Rectangle 1401 represents the projection of the cylindrical inter-vertebral cage into the image. While the long axis of the cylinder appears to be completely within the bone in this image, this may not be the case due to curvature of the anterior aspect of vertebrae 1402. FIG. 14B is an image of a three-dimensional axial CT cross section of the vertebrae. Corner 1403 of rectangle 1401 protrudes from the bone-a highly undesirable situation that cannot be reliably detected in x-ray images such as that of FIG. 14A. Accordingly, when faced with this situation, the appropriate cage length should be chosen based upon one or more axial CT images, such as that in FIG. 14B. Selection of the cage length can be performed automatically by computer 120 or semi-automatically with the input of the physician.

Once the cage length has been determined by the physician and entered into computer 120, the length value can then be used by computer 120 in properly displaying the graphical overlay in the associated two-dimensional image. The position of the surgical instrument used to hold the cage during the insertion process, as detected by tracking sensor 130, is used to calculate the position of the cage in FIG. 14A during the two-dimensional navigational process.

Although the above discussed example was with a cylindrical spinal implant, in general, the described concepts could be applied to any surgical implant.

EXAMPLE 2

Acquisition of an X-Ray View Down the Medial Axis of a Vertebral Pedicle

In certain clinical procedures, it may be desirable to acquire a fluoroscopic x-ray image view looking substantially straight down the medial axis of a vertebral pedicle. For the purposes of this example, a vertebral pedicle can be thought of as a cylinder, and the medial axis corresponds to the central axis of the cylinder.

Figure 15A:
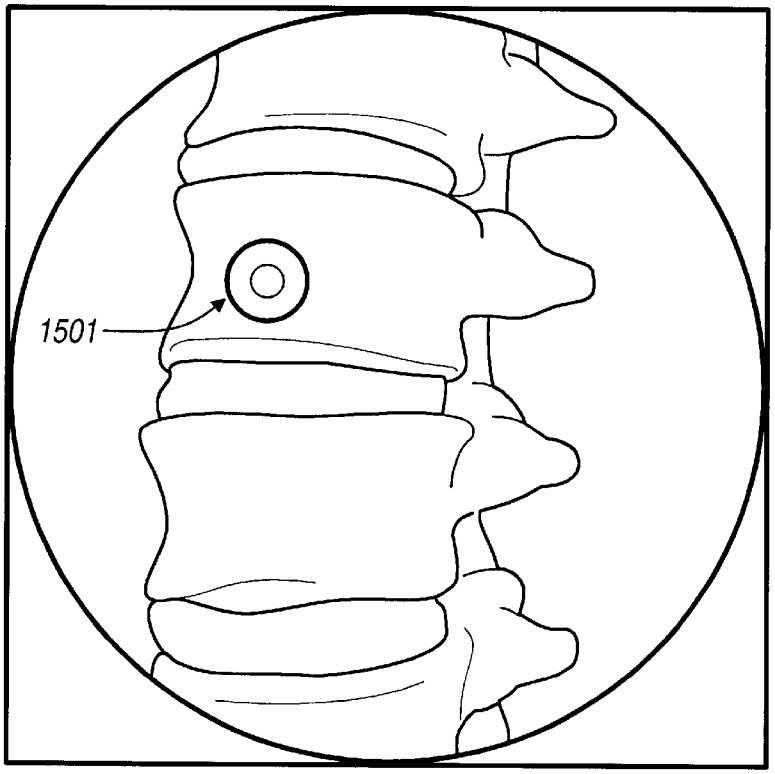
FIGS. 15A through 15C are images used in the acquisition of an x-ray view of the medial axis of a vertebral pedicle.

FIG. 15A is an x-ray image in which the view direction of the imager is aligned with the medial axis of the pedicle (i.e., the medial axis of the pedicle is into the plane of the image. In this so-called "owl's eye" view, the pedicle appears as circle 1501 within the image. It is often difficult to precisely acquire this view using only fluoroscopic x-ray images, as it is difficult it to align the view direction of imager 100 with the medial axis of the pedicle using only fluoroscopic images.

Figure 15B:
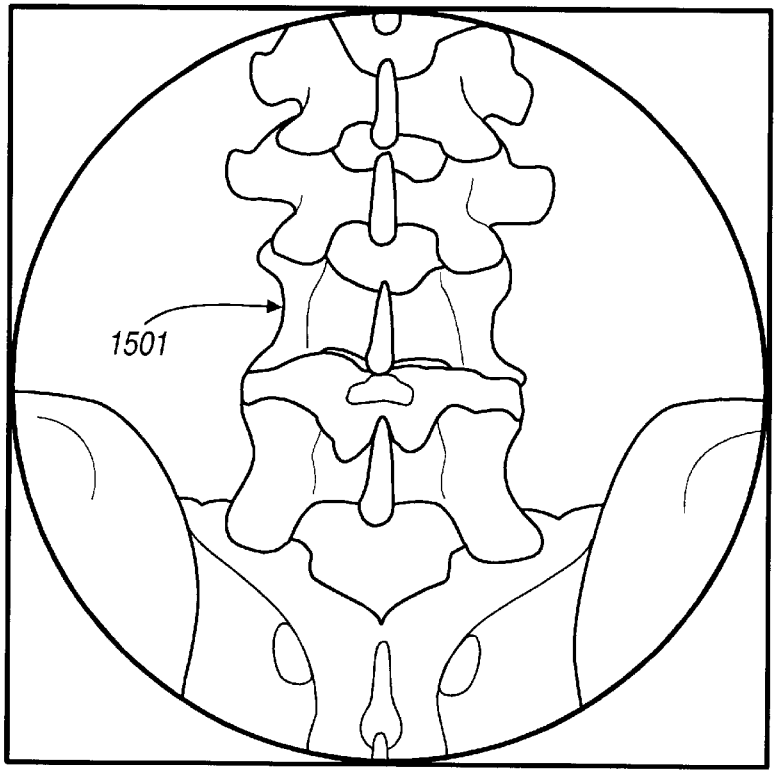

Given an anterior/posterior fluoroscopic image view of the spine, such as the one shown in FIG. 15B, and given that the mechanical axis of the fluoroscope is aligned with the patient's long axis (i.e., axis 704 in FIG. 7C), an axial CT cross section of a vertebra can be used to quickly and easily acquire a high quality owl's eye view, such as the view of FIG. 15A.

Figure 15C:
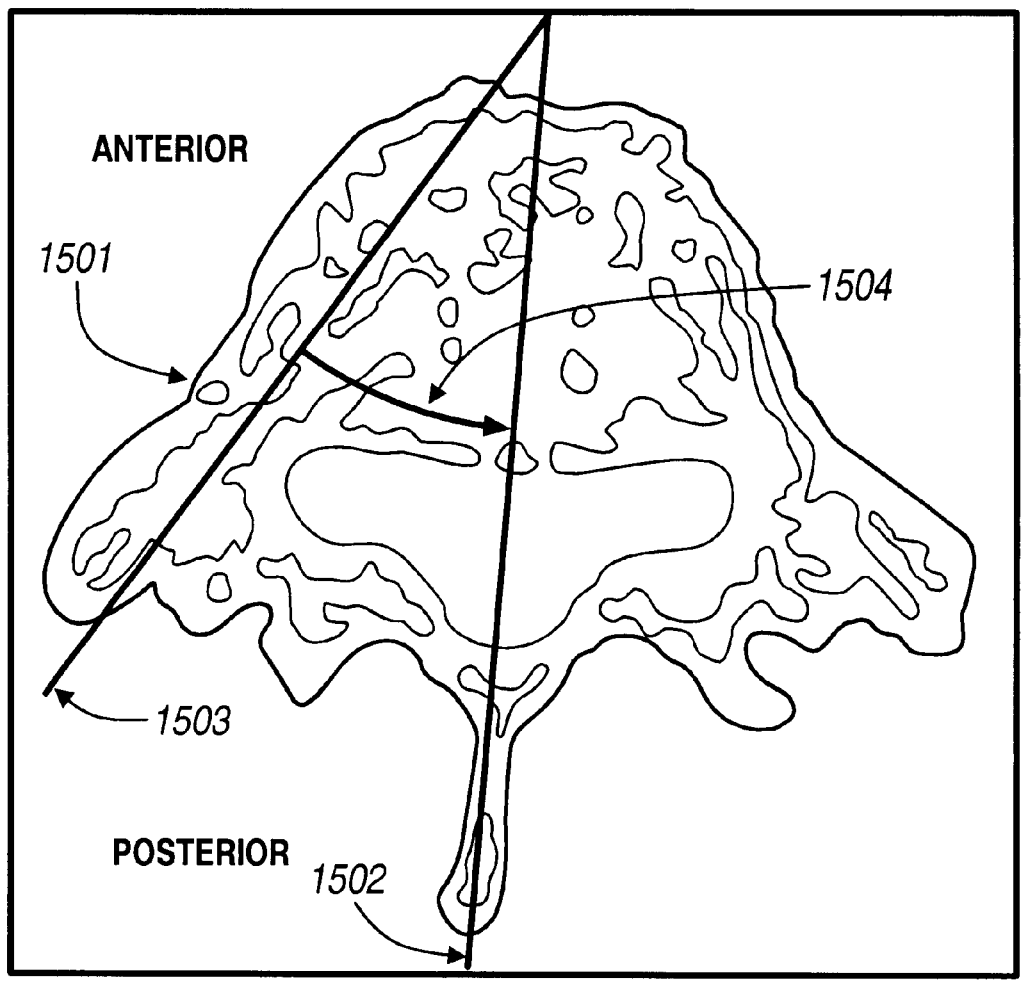

FIG. 15C is an image of an axial CT cross section of a vertebra. With this image, computer 120 or the physician may measure angle 1504 between the anterior/posterior axis 1502 and the projection of the medial axis 1503 of the pedicle 1501 into the axial plane. The physician may then rotate imager 100 by the measured angle about the mechanical rotation axis that is aligned with the patient's long axis 704. Because most fluoroscopic imagers such, as imager 100, have angle indicators, rotation by the desired amount is trivial. However, if the physician requires additional accuracy in the rotation, tracking sensor 130, because it detects the position of C-arm 103, can be used to more precisely measure the rotation angle.

EXAMPLE 3

Use of Digitally Reconstructed Radiography in the Placement of a Surgical Implant With conventional fluoroscopic x-ray image acquisition, radiation passes through a physical media to create a projection image on a radiation sensitive film or an electronic image intensifier. Given a 3D CT data set, a simulated x-ray image can also be generated using a technique known as digitally reconstructed radiography (DRR). DRR is well known in the art, and is described, for example, by L. Lemieux et al., "A Patient-to-Computed-Tomography Image Registration Method Based on Digitally Reconstructed Radiographs," Medical Physics 21(11), pp 1749–1760, November 1994.

When a DRR image is created, a fluoroscopic image is formed by computationally projecting volume elements (voxels) of the 3D CT data set onto a selected image plane. Using a 3D CT data set of a given patient, it is possible to create a DRR image that appears very similar to a corresponding x-ray image of the same patient. A requirement for this similarity is that the "computational x-ray imager" and actual x-ray imager use similar intrinsic imaging parameters (e.g., projection transformations, distortion correction) and extrinsic imaging parameters (e.g., view direction). The intrinsic imaging parameters can be derived from the calibration process.

A DRR image may be used to provide guidance to the surgeon in the problem discussed in Example 1 of appropriately placing an inter-vertebral cage in the patient. Given a 3D CT data set of two adjacent vertebrae, the physician, interacting with computer 120, may manually position a 3D CAD model of an inter-vertebral cage in a clinically desired position in the three-dimensional view of the vertebrae. The physician may then use the DRR technique to synthesize an anterior/posterior, lateral, or other x-ray view of the vertebrae showing the three-dimensional CAD model of the inter-vertebral cage. Thus, a synthetic fluoroscopic x-ray image can be created which simulates what a properly placed cage would look like after implantation.

The simulated x-ray images may be compared to the actual images taken by imager 100 during surgery. The goal of the surgeon is to position the implant such that the intra-operative images match the DRR images. For this comparison, two types of intra-operative images may preferably be used. First, conventional fluoroscope could be used to acquire an image after the inter-vertebral cage has been implanted. Second, images acquired prior to cage placement could be supplemented with superimposed graphical icons representing the measured cage position. In either case, the synthetic fluoroscopic image can be used as a template to help guide the surgeon in properly placing the inter-vertebral cage.

Although the above example was described in the context of implanting an inter-vertebral cage, implants other than the inter-vertebral cage could also be used.

EXAMPLE 4
Obtaining a Particular Two-Dimensional View Direction Using Digitally Reconstructed Radiograph Images The DRR technique can be used to provide guidance to the physician when acquiring an owl's eye view of a vertebral pedicle. Given a three-dimensional CT data set containing a vertebra and associated pedicle, the physician may use computer 120 to manually locate a three-dimensional representation of the pedicle's medial axis relative to the three-dimensional images of the vertebrae. Once this placement has been achieved, it is possible to synthesize an owl's eye view of the vertebrae based upon the view direction specified by the physician's selection of the three-dimensional medial axis. This synthetic image can then be displayed to the surgeon during surgery and used to guide the acquisition of an actual owl's eye view using the fluoroscope. By visually comparing fluoroscopic images taken while positioning the fluoroscope to the synthetic owl's eye view, the physician can acquire a true fluoroscopic image with a view direction approximately equal to the manually selected medial axis. In this manner, a high quality owl's eye view can be acquired.

Although the above example was described in the context of synthesizing a two-dimensional owl's eye view, in general, any three-dimensional view direction can be selected and a corresponding two-dimensional image synthesized and used to acquire a fluoroscopic two-dimensional image.

EXAMPLE 5
Measuring Out-Of-Plane Angles Based on Fluoroscopic Images

It may be desirable to measure the angle between the trajectory of a surgical instrument and the plane of a fluoroscopic image (such as a plane aligned with the midline of the spine 1502) during surgery using a pre-acquired fluoroscopic image. This is useful, as it is often desirable to position or implant a surgical instrument at a certain angle relative to the plane of the fluoroscopic image. For example, the surgical instrument may need to be implanted in the direction aligned with the medial axis of the pedicle 1503.

Consider the vertebral cross section shown as an axial CT image in FIG. 15C. As described above, the angle 1504 between the anterior/posterior axis of the spine 1502 and the medial axis 1503 of the pedicle can be measured from this CT image. Aligning the surgical instrument with the medial axis can be accomplished by dynamically measuring the angle between the trajectory of the surgical instrument and the plane defined by the mid-line of the spine 1502. When the dynamically measured angle matches the angle pre-obtained from the CT image, the surgical instrument is aligned.

Figure 16A:
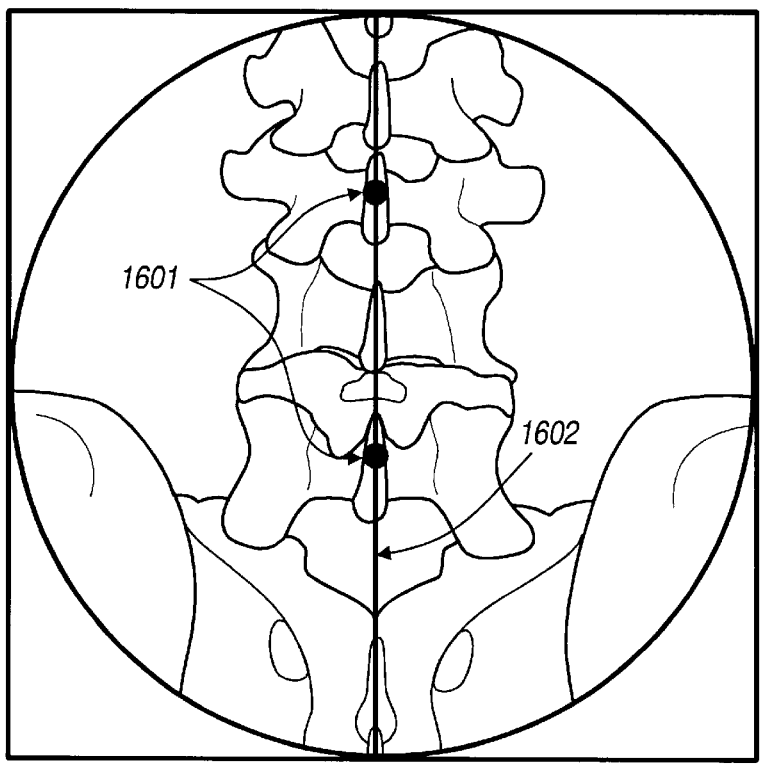
FIGS. 16A and 16B are images used to illustrate the measurement of out-of-plane angles based on fluoroscopic images.
Figure 16B:
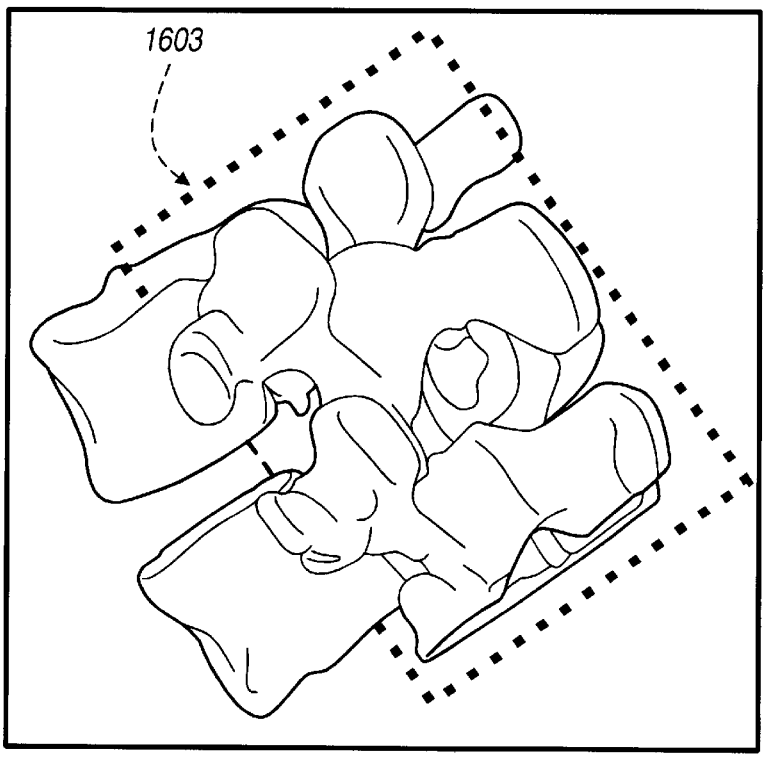

FIGS. 16A and 16B are figures respectively illustrating an anterior/posterior fluoroscopic image of the spine and a corresponding three-dimensional view of the spine. The physician defines two points along the midline of the spine, such as the points 1601 drawn on the spinous processes in FIG. 16A (in non-pathological anatomy a spinous process typically defines the midline). Computer 120 uses these points to define a line 1602 in the image, or more generally, the computer defines plane 1603 (shown in FIG. 16B) to include the two points and the linear projections of these two points dictated by the calibration transformation. More intuitively, a first order approximation of plane 1603 can be thought of as the plane passing through the two points perpendicular to the image plane. Plane 1603 defines the midline of the spine in three-dimensional space. During navigational guidance, the equation of this plane can be expressed in the coordinate system of either the dynamic reference frame 150 or the tracking sensor 130.

Using the tracking sensor 130 to measure the position and orientation (i.e., the trajectory) of the instrument 140, computer 120 then mathematically projects this trajectory onto the plane 1603. This projection will define a line passing through plane 1603. The angle between this line in plane 1603 and the instrument trajectory corresponds to the angle to be measured. In other words, the angle to be measured corresponds to the minimum angle present between the trajectory of the instrument and the plane 1603. The angle to be measured can be calculated by computer 120 and displayed to the physician either in a textual or graphical format.

In summary, as described in this example, a single fluoroscopic image can be used during surgery to position a surgical instrument at a desired trajectory relative to the plane of the fluoroscopic image. More generally, the methods described in this example relate to measuring the angle between the trajectory of a surgical instrument 140 and a plane (e.g. 1603) defined by two or more points (e.g., 1601) which have been manually or automatically selected in a fluoroscopic image. While the explanation uses a CT for clarity of the example, the measurement and display of the angle can be achieved without the use of any 3D image data.

Although the above five examples used three-dimensional patient specific data and not atlas data, in certain situations, it may be possible to use a 2D/3D registration scheme that registers non-patient specific atlas data to patient specific fluoroscopic images using deformable registration methods that do not preserve the rigidity of anatomical structure during the registration process. In this manner, the patient specific fluoroscopic images may be used to deform the atlas data to better correspond to the patient and thereby transfer atlased knowledge to the patient specific fluoroscopic images.

Conclusion

The above described systems and methods significantly extend the conventional techniques for acquiring and using x-ray images for surgical navigational guidance. It will be apparent to those skilled in the art that various modifications and variations can be made to the present invention without departing from the scope or spirit of the invention. For example although certain of the examples were described in relation to spinal examples, many other regions of body could be operated on.

Other embodiments of the invention will be apparent to those skilled in the art from consideration of the specification and practice of the invention disclosed herein. In particular, an alternative embodiment of the calibration and tracking target may allow the calibration component to be detached from the C-arm and introduced into the C-arm view for calibrations only, and then removed. It is intended that the specification and examples be considered as exemplary only, with the true scope and spirit of the invention being indicated by the following claims.

What is claimed:

1. An x-ray imaging device comprising:
   an x-ray source for generating cycles of x-ray radiation corresponding to an image acquisition cycle;
   an x-ray receiving section positioned so that x-rays emanating from the x-ray source enter the x-ray receiving section, the x-ray receiving section generating an image representing intensities of the x-rays entering the x-ray receiving section;
   a computer coupled to the x-ray receiving section;
   radiation sensors located in a path of x-rays emitted from the x-ray source, the radiation sensors detecting a beginning and an end of a radiation cycle and transmitting the detected beginning and end of the radiation cycle to the computer;
   a dynamic reference frame marker attached in a fixed position relative to a patient;
   a calibration and tracking target; and
   a tracking sensor for detecting a position, in three-dimensional space, of the dynamic reference frame marker and the calibration and tracking target; wherein the computer determines that an image acquisition cycle is erroneous when the, position of the calibration and tracking target moves relative to the position of the dynamic reference frame during an image acquisition cycle.

2. The device of claim 1, wherein the computer further comprises a display for displaying the image generated by the x-ray receiving section.

3. The device of claim 1, wherein the calibration and tracking target includes calibration markers and the calibration and tracking target is attached to the imaging device.

4. The device of claim 1, wherein the calibration and tracking target is physically separated from the x-ray source and the x-ray receiving section and calibration markers included in the calibration and tracking target are in the path of x-rays of the generated cycles of x-ray radiation.

5. An x-ray imaging device comprising:
   an x-ray source for generating cycles of x-ray radiation corresponding to an image acquisition cycle;
   an x-ray receiving section positioned so that x-rays emanating from the x-ray source enter the x-ray receiving section, the x-ray receiving section generating an image representing intensities of the x-rays entering the x-ray receiving section;
   a computer coupled to the x-ray receiving section;
   radiation sensors located in a path of x-rays emitted from the x-ray source, the radiation sensors detecting a beginning and an end of a radiation cycle and transmitting the detected beginning and end of the radiation cycle to the computer; and
   calibration markers for determining a projective transformation of the image.

6. The device of claim 5, wherein the calibration markers are used to correct image distortion.

7. An x-ray imaging device comprising:
   a rotatable C-arm support having first and second ends,
   an x-ray source positioned at the first end for initiating an imaging cycle by generating x-ray radiation;
   an x-ray receiving section positioned at the second end so that x-rays emanating from the x-ray source enter the x-ray receiving section, the x-ray receiving section generating an image representing the intensities of the x-rays entering the x-ray receiving section;
   a calibration and tracking target;
   a tracking sensor for detecting a position, in three-dimensional space, of the calibration and tracking target;
   a computer communicating with the x-ray receiving section and the tracking sensor, the computer detecting motion of the C-arm based on changes in the position detected by the tracking sensor;
   a dynamic reference frame marker attached in a fixed position relative to a patient, the tracking sensor detecting the position, in three-dimensional space, of the dynamic reference frame marker; and
   means for detecting a beginning and an end of an imaging cycle and transmitting indications of the detected beginning and end of the radiation cycle to the computer, and the computer determining that an image acquisition cycle is erroneous when the position of the tracking target moves with respect to the dynamic reference frame marker during the imaging cycle.

8. A surgical instrument navigation system comprising;
   a computer processor;
   a tracking sensor for sensing three-dimensional position information of a surgical instrument and transmitting the position information to the computer processor;
   a memory coupled to the computer processor, the memory including computer instructions that when executed by the computer processor cause the processor to generate an icon representing the surgical instrument and to overlay the icon on a pre-acquired x-ray image, the icon of the surgical instrument representing the real-time position of the surgical instrument projected into the pre-acquired x-ray image and the icon being generated as a first representation when the surgical instrument is positioned such that it is substantially viewable in the plane of the pre-acquired image and the icon being automatically generated as a second representation when a distance in the pre-acquired image between a tip and tail of the surgical instrument becomes smaller than a pre-determined distance such that the surgical instrument is substantially perpendicular to the plane of the pre-acquired image; and
   a display coupled to the processor for displaying the generated icon as one of either the first and second representations superimposed on the pre-acquired image.

9. The computer system of claim 8, wherein the icon is superimposed on multiple pre-acquired images.

10. The computer system of claim 8, wherein the second representation includes first and second cross-hair icons, the center of the first icon representing one end of the surgical instrument and the center of the second icon representing an opposite end of the surgical instrument.

11. A surgical instrument navigation system comprising:
a computer processor;
a tracking sensor for sensing three-dimensional position information of a surgical instrument and transmitting the position information to the computer processor;
a memory coupled to the computer processor, the memory including computer instructions that when executed by the computer processor cause the processor to generate an icon representing the surgical instrument positioned in a pre-acquired image of a patient's anatomy, the icon of the surgical instrument including a first portion corresponding to an actual position of the surgical instrument and a second portion corresponding to a current projection of the surgical Instrument along a line given by a current trajectory of the surgical instrument where a length of the second portion is selectable by a user of the surgical instrument navigation system; and
a display coupled to the processor for displaying the generated icon superimposed on the pre-acquired image.

12. The computer system of claim 11, wherein the icon is superimposed on multiple pre-acquired images.

13. A surgical instrument navigation system comprising,
a rotatable C-arm including an x-ray source and an x-ray receiving section for acquiring x-ray images of a patient, the C-arm being rotatable about one of a plurality of mechanical axes;
a computer processor coupled to the rotatable C-arm;
a memory coupled to the computer processor, the memory storing the x-ray images acquired by the rotatable C-arm and computer instructions that when executed by the computer processor cause the computer processor to generate a line representing a projection of a plane substantially parallel to one of the plurality of the mechanical axes of the C-arm into the x-ray image, the line enabling visual alignment of the one of the plurality of mechanical axes of the C-arm with an axis relating complimentary x-ray images; and
a display coupled to the processor for displaying at least a portion of the generated line superimposed on the x-ray image, wherein the line displayed on the display enables visual alignment of the C-arm with the complimentary axis before the complimentary x-ray image is acquired.

14. The system of claim 13, further comprising:
a tracking target attached to the rotatable C-arm; and
a tracking sensor for detecting a position, in three-dimensional space, of the tracking target, wherein the computer calculates an amount of rotation of the C-arm based on changes in the position detected by the tracking sensor.

15. A system for defining a surgical plan comprising:
an x-ray imaging device;
a surgical instrument;
a tracking sensor for detecting a position, in three-dimensional space, of the surgical Instrument;
a computer processor in communication with the tracking sensor for calculating a projection of a trajectory of the surgical instrument a distance ahead of an actual location of the surgical instrument; and
a display coupled to the processor for displaying a pre-acquired x-ray image overlaid with an iconic representation of the surgical instrument and a calculated projection of the trajectory of the surgical instrument, wherein a length of the projection of the surgical instrument changes based upon an input received by a user.

16. A method of defining a surgical plan comprising:
acquiring an image of a patient's anatomy;
sensing three-dimensional position information of a surgical instrument;
generating a graphical icon representing the surgical instrument positioned in a pre-acquired image of the patient's anatomy, the icon of the surgical instrument including a first portion corresponding to a position of the surgical instrument in space and a second portion corresponding to a current projection of the surgical instrument along a line given by a current trajectory of the surgical instrument;
selecting a length of the second portion corresponding to the current trajectory of the surgical instrument; and
displaying the generated icon superimposed on the pre-acquired image.

17. The method of claim 16, further comprising freezing at least the first or second portion of the iconic representation of the surgical instrument in the x-ray image.

18. The method of claim 16, wherein the icon is superimposed on multiple pre-acquired images.

19. A method of representing a real-time position of a surgical instrument in a pre-acquired x-ray image comprising:
generating an icon of a surgical instrument and overlaying the icon on the pre-acquired x-ray image, the icon of the surgical instrument representing the real-time position of the surgical instrument projected into the pre-acquired x-ray image;
representing the icon as a first representation when the surgical instrument is positioned such that it is substantially viewable in a plane of the pre-acquired image; and
automatically representing the icon as a second representation when a distance in the pre-acquired image between a tip and a tail of the surgical instrument becomes smaller than a pre-determined distance such that it is substantially perpendicular to, the plane of the pre-acquired image.

20. A method of detecting an error in an x-ray process comprising:
generating cycles of x-ray radiation corresponding to an image acquisition cycle, the cycles being generated by an x-ray imager and passing through calibration markers of a calibration and tracking target;
generating an image of a patient's anatomy defined by intensities of the x-rays in the cycle of the x-ray radiation;
detecting a beginning and an end of a radiation cycle;
detecting a position of the calibration and tracking target and the patient; and
determining that the image acquisition cycle is erroneous when the position of the tracking target relative to the position of the patient moves between the beginning and the end of the radiation cycle.

21. A system of defining a surgical plan comprising:
means for sensing three-dimensional position information of a surgical instrument;
means for generating a graphical icon representing the surgical instrument positioned in a pre-acquired image of a patient's anatomy, the icon of the surgical instrument including a first portion corresponding to a position of the surgical instrument in space and a second portion corresponding to a projection of the surgical instrument along a line given by a current trajectory of the surgical instrument;

means for selecting a length of the second portion corresponding to the current trajectory of the surgical instrument; and means for displaying the generated icon superimposed on the pre-acquired image.

22. A system for representing a real-time position of a surgical instrument in a pre-acquired x-ray image comprising:

means for generating an icon of a surgical instrument and overlaying the icon on the pre-acquired x-ray image, the icon of the surgical instrument representing the real-time position of the surgical instrument projected into the pre-acquired x-ray image;

means for representing the icon as a first representation when the surgical instrument is positioned such that it is substantially viewable in a plane of the pre-acquired image; and means for representing the icon as a second representation when a distance in the pre-acquired image between a tip and a tail of the surgical instrument becomes smaller than a predetermined distance such that it is substantially perpendicular to the plane of the pre-acquired image.

23. An x-ray imaging device comprising:

means for generating cycles of x-ray radiation corresponding to an image acquisition cycle;

means for generating an image representing intensities of the x-rays entering an x-ray receiving section;

means for detecting a beginning and an end of a radiation cycle and transmitting the detected beginning and end of the radiation cycle to a computer;

a dynamic reference frame marker attached in a fixed position relative to a patient;

a calibration and tracking target; and a tracking sensor for detecting a position, in three-dimensional space, of the dynamic reference frame marker and the calibration and tracking target; wherein the computer determines that an image acquisition cycle is erroneous when the position of the calibration and tracking target moves relative to the position of the dynamic reference frame during an image acquisition cycle.

* * * * *